(12) United States Patent
Russell et al.

(10) Patent No.: US 6,562,609 B1
(45) Date of Patent: May 13, 2003

(54) CHOLESTEROL 25-HYDROXYLASE

(75) Inventors: David W. Russell, Dallas, TX (US); Erik G. Lund, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/177,419

(22) Filed: Oct. 22, 1998

(51) Int. Cl.[7] .......................... C12N 9/02; C12N 15/53; C12N 15/63; C12N 15/79; C12Q 1/26
(52) U.S. Cl. .......................... 435/189; 435/6; 435/69.1; 435/252.3; 435/320.1; 536/23.2
(58) Field of Search .......................... 435/6, 189, 471, 435/320.1, 69.1, 252.3; 530/350; 536/23.2

(56) References Cited

U.S. PATENT DOCUMENTS 5,753,431 A * 5/1998 Chiang .......................... 435/6

FOREIGN PATENT DOCUMENTS

JP   9-40697   *   2/1997

OTHER PUBLICATIONS

Li, L., et al., The Journal of Biological Chemistry, vol. 271, "Characterization of yeast sterol oxidase (ERG25) and identification of a human homologue", pp. 16926–16933, 1996.*

Bard, M. et al., 1996, "Cloning and characterization of ERG25, the *Saccharomyces cerevisiae* gene encoding C–4 sterol methyl oxidase", Proceedings of the National Academy of Sciences, U.S.A., vol. 93, pp. 186–190.*

Entian, K. D., et al., 1996, Protein Sequence Database Accession No. S64354, *Saccharomyces cerevisiae* ERG25 protein amino acid sequence translated from DNA.*

Bevan, M., et al., 1996, EMBL/GENBANK/DDBJ Database Accession No. O49656, *Arabidopsis thaliana* predicted protein amino acid sequence translated from DNA.*

Li, L., and Kaplan, J., 1996, "Characterization of Yeast Methyl Sterol oxidase (ERG25) and Identification of a Human Homologue", The Journal of Biological Chemistry, vol. 271, No. 28, pp. 16927–16933.*

Hillier, L., et al., 1996, EMBL/EST Database Accession No. N45640, "Homo sapiens cDNA clone IMAGE:279562 5', mRNA sequence", The WashU–Merck EST Project, NID g1186806.*

Hillier, L., et al., 1996, EMBL/EST Database Accession No. N51873, "Homo sapiens cDNA clone IMAGE:282128 3', mRNA sequence", The WashU–Merck EST Project, NID g1193039.*

Hillier, L., et al., 1996, EMBL/EST Database Accession No. N51903, "Homo sapiens cDNA clone IMAGE:282175 3', mRNA sequence", The WashU–Merck EST Project, NID g1193069.*

Hillier, L., et al., 1996, EMBL/EST Database Accession No. W01328, "Homo sapiens cDNA clone IMAGE:278495 5' similar to contains element mER22 repetitive element, mRNA sequence", The WashU–Merck EST Project, NID g1273328.*

Marra, M., et al., 1997, EMBL/EST Database Accession No. AA285796, "Mus musculus cDNA clone IMAGE:764198 5', mRNA sequence", The WashU–HHMI Mouse EST Project, NID g1931972.*

Marra, M., et al., 1997, EMBL/EST Database Accession No. AA289153, "Mus musculus cDNA clone IMAGE:750976 5', mRNA sequence", The WashU–HHMI Mouse EST Project, NID g1936425.*

National Cancer Institute, Cancer Gene Anatomy Project, 1998, EMBL/EST Database Accession No. AI081548, "Homo sapiens cDNA clone IMAGE:1555741 3', mRNA sequence", NCI–CGAP Tumor Gene Index, NID g3418340.*

Zaharias, G. G., et al., 1998, EMBL/EST Database Accession No. AQ225427, "Human Genomic Sperm Library D Homo sapiens genomic clone", NID g3650656.*

Database EMBL, AC AQ225427, Sep. 28, 1998, Mahairas G G et al: "HS_2003_B1_EO3_T7 CIT Approved Human Genomic Sperm Library D Homo sapiens genomic clone Plate=203 Col=9 Row=J, genomic survey sequence".

Database EMBL, AC AI169398, Oct. 8, 1998, Lee N H et al: "EST215244 Normalized rat kidney, Bento Soares Rattus sp. cDNA clone RKIBR78 3' end, mRNA sequence."

* cited by examiner

Primary Examiner—Ponnathapu Achutamurthy
Assistant Examiner—William W. Moore
(74) Attorney, Agent, or Firm—Richard Aron Osman

(57) ABSTRACT

The invention provides methods and compositions relating to cholesterol 25-hydroxylase polypeptides having cholesterol 25-hydroxylase-specific structure and activity, related polynucleotides and modulators of cholesterol 25-hydroxylase function and serum cholesterol. The invention provides isolated cholesterol 25-hydroxylase hybridization probes and primers capable of specifically hybridizing with natural cholesterol 25-hydroxylase genes, cholesterol 25-hydroxylase-specific binding agents such as specific antibodies, agonists and antagonists, and methods of making and using the subject compositions in diagnosis (e.g. genetic hybridization screens for cholesterol 25-hydroxylase transcripts), therapy (e.g. cholesterol 25-hydroxylase inhibitors to modulate serum cholesterol) and in the biopharmaceutical industry (e.g. as immunogens, reagents for isolating natural 25-hydroxylase genes and transcripts, reagents for screening chemical libraries for lead pharmacological agents, etc.).

28 Claims, No Drawings

SEQUENCE LISTING

<160> NUMBER OF SEQ ID NOS: 16

<210> SEQ ID NO 1
<211> LENGTH: 1406
<212> TYPE: DNA
<213> ORGANISM: human
<220> FEATURE:
<221> NAME/KEY: CDS
<222> LOCATION: (11)..(826)

<400> SEQUENCE: 1

```
cagcctcgca atg agc tgc cac aac tgc tcc gac ccc cag gtc ctt tgc        49
          Met Ser Cys His Asn Cys Ser Asp Pro Gln Val Leu Cys
           1               5                  10
```

```
agc tcc ggg cag ctg ttc ctg cag ccc ctc tgg gac cac ctg agg agc        97
Ser Ser Gly Gln Leu Phe Leu Gln Pro Leu Trp Asp His Leu Arg Ser
 15                  20                  25 tgg gag gcc ctc cta cag tcg ccc ttc ttc ccg gtc atc ttc tcc atc       145
Trp Glu Ala Leu Leu Gln Ser Pro Phe Phe Pro Val Ile Phe Ser Ile
 30                  35                  40                  45 acc aca tac gtg ggc ttt tgc ctg ccc ttc gtg gtc ctg gat atc ctg       193
Thr Thr Tyr Val Gly Phe Cys Leu Pro Phe Val Val Leu Asp Ile Leu
                 50                  55                  60 tgc tcc tgg gtg ccc gcc ctg cgg cgc tac aag atc cac cct gac ttc       241
Cys Ser Trp Val Pro Ala Leu Arg Arg Tyr Lys Ile His Pro Asp Phe
                 65                  70                  75 tcg cca tcc gcg cag cag ctg cta cct tgc ctg ggg cag acc ctc tac       289
Ser Pro Ser Ala Gln Gln Leu Leu Pro Cys Leu Gly Gln Thr Leu Tyr
         80                  85                  90 cag cat gtg atg ttt gtg ttc ccc gtg acg ctg ctg cat tgg gcc cgc       337
Gln His Val Met Phe Val Phe Pro Val Thr Leu Leu His Trp Ala Arg
         95                 100                 105 agc ccg gcc ctc ctg ccc cac gaa gct ccc gag ctg ctc ctg ctg ctg       385
Ser Pro Ala Leu Leu Pro His Glu Ala Pro Glu Leu Leu Leu Leu Leu
110                 115                 120                 125 cac cac atc ctg ttc tgc ctg cta ctc ttc gac atg gag ttc ttc gtg       433
His His Ile Leu Phe Cys Leu Leu Leu Phe Asp Met Glu Phe Phe Val
                130                 135                 140 tgg cac ctg ctg cac cac aag gtg ccc tgg ctg tac cgc acc ttc cac       481
Trp His Leu Leu His His Lys Val Pro Trp Leu Tyr Arg Thr Phe His
                145                 150                 155 aag gtg cac cac cag aac tcg tcc tcg ttc gcg ctg gca acg cag tat       529
Lys Val His His Gln Asn Ser Ser Ser Phe Ala Leu Ala Thr Gln Tyr
                160                 165                 170 atg agc gtc tgg gaa ctg ttt tct ttg ggc ttc ttc gac atg atg aac       577
Met Ser Val Trp Glu Leu Phe Ser Leu Gly Phe Phe Asp Met Met Asn
175                 180                 185 gtc aca ctg ctc ggg tgc cac ccg ctc acc acc ctg acc ttc cac gtg       625
Val Thr Leu Leu Gly Cys His Pro Leu Thr Thr Leu Thr Phe His Val
190                 195                 200                 205 gtc aac atc tgg ctt tcc gtg gag gac cac tcc ggc tac aac ttc cct       673
Val Asn Ile Trp Leu Ser Val Glu Asp His Ser Gly Tyr Asn Phe Pro
                210                 215                 220 tgg tcc act cac aga ctg gtg ccc ttc ggg tgg tac ggg ggt gtg gtg       721
Trp Ser Thr His Arg Leu Val Pro Phe Gly Trp Tyr Gly Gly Val Val
                225                 230                 235 cac cac gac ctg cat cac tct cac ttt aac tgc aac ttc gct ccg tac       769
His His Asp Leu His His Ser His Phe Asn Cys Asn Phe Ala Pro Tyr
                240                 245                 250 ttt aca cac tgg gac aaa ata ctg gga acg ctg cgg act gca tct gtc       817
Phe Thr His Trp Asp Lys Ile Leu Gly Thr Leu Arg Thr Ala Ser Val
255                 260                 265 cca gcg cgg tgatgtggct gcggtgggtg cccctaagac tcgggactgc               866
Pro Ala Arg
270 tgtgcctttc acacttgaat gaagagaaac acctgagcta tatattttt taaagcaact      926 aacttattgc tttatgttta tctatgaaaa ccatagataa aatctgatgc atttttgtaa     986 tctgacaaag taatttacat actgtttgtg tatcaataca attttgtgtt cttggtattc    1046 ttagtctagc tcacctcaat agccttgaat cctgcatatg aattagacat tcatcactgg   1106 catatttaga atatctctaa aaggacttgt ttgtagaata aggaattttc tatgtttcaa   1166 agtgttctaa aacctggcta aaagaatgta tttttgtgga tggtgttgac ttctgactct   1226
```

```
aaaagcaatc aaacatgttt ctgctggaca gtgaccaaga attatagtac cttcttatat    1286
ttttttatag aactgtatat ttattttgaa agaaatgtta ttcgtgcttt aaaaaggaaa    1346
aaaaaccatg aatcaaataa gtattgactt ccgtttcact ggtattttga ctgataaaaa    1406
```

```
<210> SEQ ID NO 2
<211> LENGTH: 272
<212> TYPE: PRT
<213> ORGANISM: human

<400> SEQUENCE: 2

Met Ser Cys His Asn Cys Ser Asp Pro Gln Val Leu Cys Ser Ser Gly
 1               5                  10                  15

Gln Leu Phe Leu Gln Pro Leu Trp Asp His Leu Arg Ser Trp Glu Ala
            20                  25                  30

Leu Leu Gln Ser Pro Phe Phe Pro Val Ile Phe Ser Ile Thr Thr Tyr
        35                  40                  45

Val Gly Phe Cys Leu Pro Phe Val Leu Asp Ile Leu Cys Ser Trp
    50                  55                  60

Val Pro Ala Leu Arg Arg Tyr Lys Ile His Pro Asp Phe Ser Pro Ser
65                  70                  75                  80

Ala Gln Gln Leu Leu Pro Cys Leu Gly Gln Thr Leu Tyr Gln His Val
                85                  90                  95

Met Phe Val Phe Pro Val Thr Leu Leu His Trp Ala Arg Ser Pro Ala
            100                 105                 110

Leu Leu Pro His Glu Ala Pro Glu Leu Leu Leu Leu His His Ile
        115                 120                 125

Leu Phe Cys Leu Leu Leu Phe Asp Met Glu Phe Phe Val Trp His Leu
    130                 135                 140

Leu His His Lys Val Pro Trp Leu Tyr Arg Thr Phe His Lys Val His
145                 150                 155                 160

His Gln Asn Ser Ser Ser Phe Ala Leu Ala Thr Gln Tyr Met Ser Val
                165                 170                 175

Trp Glu Leu Phe Ser Leu Gly Phe Phe Asp Met Met Asn Val Thr Leu
            180                 185                 190

Leu Gly Cys His Pro Leu Thr Thr Leu Thr Phe His Val Val Asn Ile
        195                 200                 205

Trp Leu Ser Val Glu Asp His Ser Gly Tyr Asn Phe Pro Trp Ser Thr
    210                 215                 220

His Arg Leu Val Pro Phe Gly Trp Tyr Gly Gly Val Val His Asp
225                 230                 235                 240

Leu His His Ser His Phe Asn Cys Asn Phe Ala Pro Tyr Phe Thr His
                245                 250                 255

Trp Asp Lys Ile Leu Gly Thr Leu Arg Thr Ala Ser Val Pro Ala Arg
            260                 265                 270

<210> SEQ ID NO 3
<211> LENGTH: 2951
<212> TYPE: DNA
<213> ORGANISM: Mouse
<220> FEATURE:
<221> NAME/KEY: CDS
<222> LOCATION: (1183)..(2076)
<220> FEATURE:
<223> OTHER INFORMATION: n signifies a, t, c or g.

<400> SEQUENCE: 3
```

-continued

| | |
|---|---:|
| tcccccccccc cagggggac tggcagcagg ctcctagagc tacaatccct gttttctttg | 60 |
| gaaaataaca caagaaacac aagcttgtat aagactatgt tagcttccag cagagaaaag | 120 |
| cagctgtaaa gacacaaatt caagaaggaa accctgggag aatggcccct ggctttcctc | 180 |
| tgggatcttc tgtgccgtgt atccgctacc cggggctgat ttctgtgctc cactctctag | 240 |
| ggcactctcc ttggatatag tactgacctc ctgtgctcag tccctggacg atcagtccca | 300 |
| gtgtctgaaa gggtatccag gagttgagga gtagggaaca actgagggtt ggtaaaagtc | 360 |
| ggagcctgag ggacctctaa ggaaatggca ggggagatga gacatgttcc gggaggctat | 420 |
| gagattgctc agatcttctt ctccactggc ctttgcggtt tggcccaatc gagtgagcct | 480 |
| ttacgggtgt taagcctccg ttctccaacc cagagcaaag gctggcagtg ctgccctctt | 540 |
| gaccgctgtc ttgcaggatc tgatctctgc tcttgacacc gcgggcttta agggcaccag | 600 |
| agcgggagag tcgtccgcgc caaaaggctg cgagcctgac tgctcttttt tggaggatgc | 660 |
| caggttccct ctcctacagg actcaatccc tgtctgcaac ggacccagta ccagcactgt | 720 |
| ggcgtgaggt acgcacactc agagtccccc aaggtgtaga ataagtcttt aaacagtcaa | 780 |
| aaacagatat tttaaaaccc agggaattct gctttggttg agaaacagcg ccttctgaga | 840 |
| gcgaagaact cattagtttt tagcggtgat ggcgggtgaa ctgtcccaag cagaatcgc | 900 |
| tctctcctgt gtcattagta catcagctga aaggcaagca aacagttctt tacgtctggg | 960 |
| aaagggcttt aaggcccgct gcttgcgtga agggagatt tgatgcagct ataaaccagg | 1020 |
| acatagacag gaacaaaatt cgggttattt aagcaaaatt ctttagcagg gaaagggagg | 1080 |
| tgggaaggag acggaagggt gacgtcactg gggggagtgg ccacagtctt aagaaaagtc | 1140 |
| ggcggggctg gggagaccac aattgtggga catagtctca gc atg ggc tgc tac | 1194 |
|                                                                                        Met Gly Cys Tyr<br>                                                                                                1 | |
| aac ggt tcg gag ctc caa gac ctg ggc tgt tcc agc cag ctg ctc ctg<br>Asn Gly Ser Glu Leu Gln Asp Leu Gly Cys Ser Ser Gln Leu Leu Leu<br> 5                     10                  15                    20 | 1242 |
| cag ccc ctc tgg gac acc ata agg aca agg gag gcg ttc acg cgc tca<br>Gln Pro Leu Trp Asp Thr Ile Arg Thr Arg Glu Ala Phe Thr Arg Ser<br>                25                      30                      35 | 1290 |
| ccc atc ttc cca gtc acc ttt tct atc atc act tac gtg ggc ttc tgc<br>Pro Ile Phe Pro Val Thr Phe Ser Ile Ile Thr Tyr Val Gly Phe Cys<br>              40                      45                      50 | 1338 |
| cta ccg ttc gtg gtg ctg gac gtc ctg tat ccc tgg gtc ccc atc ctg<br>Leu Pro Phe Val Val Leu Asp Val Leu Tyr Pro Trp Val Pro Ile Leu<br>        55                      60                      65 | 1386 |
| cga cgc tac aag atc cac ccg gac ttc tcg cct tcc gta aag cag ctt<br>Arg Arg Tyr Lys Ile His Pro Asp Phe Ser Pro Ser Val Lys Gln Leu<br>    70                      75                      80 | 1434 |
| ctg cct tgc ctg ggg ctg aca ctc tac cag cac ctg gtg ttc gtg ttc<br>Leu Pro Cys Leu Gly Leu Thr Leu Tyr Gln His Leu Val Phe Val Phe<br>85                    90                  95                  100 | 1482 |
| ccg gtg acg ctg ctg cac tgg gtg cgc agc ccg gcg ctc ctc ccc cag<br>Pro Val Thr Leu Leu His Trp Val Arg Ser Pro Ala Leu Leu Pro Gln<br>              105                    110                  115 | 1530 |
| gag gcc cct gag ctc gtc cag ctc cta agt cac gtc ctg atc tgc ctg<br>Glu Ala Pro Glu Leu Val Gln Leu Leu Ser His Val Leu Ile Cys Leu<br>        120                    125                  130 | 1578 |
| ctg ctc ttc gac acc gag atc ttc gcg tgg cac ctg ctg cac cat aag<br>Leu Leu Phe Asp Thr Glu Ile Phe Ala Trp His Leu Leu His His Lys<br>              135                    140                  145 | 1626 |
| gtg ccc tgg ctg tac cgc acc ttc cac aag gtg cat cac cag aac tcg | 1674 |

-continued

| | | |
|---|---|---|
| Val Pro Trp Leu Tyr Arg Thr Phe His Lys Val His His Gln Asn Ser<br>150                      155                      160 | | |
| tcc tcc ttc gcg ctg gcg acc caa tac atg agc ttc tgg gag ctg ctt<br>Ser Ser Phe Ala Leu Ala Thr Gln Tyr Met Ser Phe Trp Glu Leu Leu<br>165                  170                  175                  180 | 1722 |
| tcg ctg acc ttc ttc gac gtg ctg aac gtc gcg gtg ctt cgg tgt cac<br>Ser Leu Thr Phe Phe Asp Val Leu Asn Val Ala Val Leu Arg Cys His<br>                  185                  190                  195 | 1770 |
| cca ctc acc atc ttt acc ttt cac gtg att aac atc tgg ctg tcg gtg<br>Pro Leu Thr Ile Phe Thr Phe His Val Ile Asn Ile Trp Leu Ser Val<br>        200                  205                  210 | 1818 |
| gag gac cac tcg ggc tat gac ttc ccg tgg tcc act cac aga ctt gtg<br>Glu Asp His Ser Gly Tyr Asp Phe Pro Trp Ser Thr His Arg Leu Val<br>215                      220                      225 | 1866 |
| ccc ttt ggc tgg tac ggg ggc gtg gct cac cac gac atg cat cac tct<br>Pro Phe Gly Trp Tyr Gly Gly Val Ala His His Asp Met His His Ser<br>                230                  235                  240 | 1914 |
| cag ttt aac tgc aat ttt gct cct tac ttc aca cac tgg gac aaa atg<br>Gln Phe Asn Cys Asn Phe Ala Pro Tyr Phe Thr His Trp Asp Lys Met<br>245                      250                  255                  260 | 1962 |
| ctg ggc act ctg cgg tcc gcg ccc ctg cca gag agc ctt tgc gcc tgc<br>Leu Gly Thr Leu Arg Ser Ala Pro Leu Pro Glu Ser Leu Cys Ala Cys<br>                  265                  270                  275 | 2010 |
| ggt gag cgc tgc gtg aac tcc aga gag cga tgc gct gta cac ttg atc<br>Gly Glu Arg Cys Val Asn Ser Arg Glu Arg Cys Ala Val His Leu Ile<br>        280                  285                  290 | 2058 |
| cag aag aag aaa cag act tgagttactt tattagaagt ttgtaacttt<br>Gln Lys Lys Lys Gln Thr<br>        295 | 2106 |
| taaagtgatg cacactgcta taaatctaa tgttgttttt gcagcctgac aaagtaattt | 2166 |
| atataatgtt tctatgtgaa tttaattgtg gtcttggtgt taaatttcaa cttatcccag | 2226 |
| tgtcattgac tccaggacac aaggtagaca ttcagcgtgg tgtatttgaa tcattatgat | 2286 |
| ntctgaaatg atttgtttct agaaccaaga cttccctatg tatgaaatcg cactggaact | 2346 |
| gggctctaac ctcacatgtt gagagaagac ctgatttctg actctttaaa taatcaaatt | 2406 |
| tgttcctgct gggcagtgac caaggttata gtatattttt tctacttttg aatgaaatga | 2466 |
| tatatttata ttgaaaaaag ttttatttgt attttaaaaa taaaagaac atgaactaaa | 2526 |
| caagcattag ctcctggtgg gcctgatgaa ttaaaaaaaa aactaaaaag gaagtgtgtg | 2586 |
| tgtgtgtgtg tgtgtgtgtg tgtgtgtgtg tgtgtgtgtg tctgtggctt ctcagtgttc | 2646 |
| tttgaaacat ctaccactct tgccatggca aaaacaattt ggtgtcatgt attgggcggg | 2706 |
| ggggctaggg aataactttg ggaanaagct agggctact gactgcttat tcccactgct | 2766 |
| ttttgtctgg ttttgacata aaacccgtg aaaaaccgct ctgtangtta ctttnctang | 2826 |
| ggannaanaa cactctcttc tgtattgttg gantgctatg cgtagggtaa ctaaaaatca | 2886 |
| naattncccc ttgataaccc atttagtgca ttagggaaac tgaaaaacac ccccatttta | 2946 |
| agggt | 2951 |

<210> SEQ ID NO 4
<211> LENGTH: 298
<212> TYPE: PRT
<213> ORGANISM: Mouse

<400> SEQUENCE: 4

Met Gly Cys Tyr Asn Gly Ser Glu Leu Gln Asp Leu Gly Cys Ser Ser
1                 5                    10                  15

```
Gln Leu Leu Gln Pro Leu Trp Asp Thr Ile Arg Thr Arg Glu Ala
         20                  25                  30
Phe Thr Arg Ser Pro Ile Phe Pro Val Thr Phe Ser Ile Ile Thr Tyr
         35                  40                  45
Val Gly Phe Cys Leu Pro Phe Val Leu Asp Val Leu Tyr Pro Trp
 50                  55                  60
Val Pro Ile Leu Arg Arg Tyr Lys Ile His Pro Asp Phe Ser Pro Ser
 65                  70                  75                  80
Val Lys Gln Leu Leu Pro Cys Leu Gly Leu Thr Leu Tyr Gln His Leu
                 85                  90                  95
Val Phe Val Phe Pro Val Thr Leu Leu His Trp Val Arg Ser Pro Ala
                100                 105                 110
Leu Leu Pro Gln Glu Ala Pro Glu Leu Val Gln Leu Leu Ser His Val
                115                 120                 125
Leu Ile Cys Leu Leu Leu Phe Asp Thr Glu Ile Phe Ala Trp His Leu
 130                 135                 140
Leu His His Lys Val Pro Trp Leu Tyr Arg Thr Phe His Lys Val His
145                 150                 155                 160
His Gln Asn Ser Ser Ser Phe Ala Leu Ala Thr Gln Tyr Met Ser Phe
                165                 170                 175
Trp Glu Leu Leu Ser Leu Thr Phe Phe Asp Val Leu Asn Val Ala Val
                180                 185                 190
Leu Arg Cys His Pro Leu Thr Ile Phe Thr Phe His Val Ile Asn Ile
            195                 200                 205
Trp Leu Ser Val Glu Asp His Ser Gly Tyr Asp Phe Pro Trp Ser Thr
 210                 215                 220
His Arg Leu Val Pro Phe Gly Trp Tyr Gly Gly Val Ala His His Asp
225                 230                 235                 240
Met His His Ser Gln Phe Asn Cys Asn Phe Ala Pro Tyr Phe Thr His
                245                 250                 255
Trp Asp Lys Met Leu Gly Thr Leu Arg Ser Ala Pro Leu Pro Glu Ser
                260                 265                 270
Leu Cys Ala Cys Gly Glu Arg Cys Val Asn Ser Arg Glu Arg Cys Ala
            275                 280                 285
Val His Leu Ile Gln Lys Lys Lys Gln Thr
290                 295

<210> SEQ ID NO 5
<211> LENGTH: 1106
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 5
acacaacctt gtataagact atgttagctt ccagcagaga aaagcagctg taaagacaca      60
aattcaagaa ggaaaccctg ggagaatggc ccctggcttt cctctgggat cttctgtgcc    120
gtgtatccgc tacccggggc tgatttctgt gctccactgt ctagggcact ctccttggat    180
atagtactga cctcctgtgc tcagtccctg gacgatcagt cccagtgtct gaaagggtat    240
ccaggagttg aggagtaggg aacaactgag ggttggtaaa agtcggagcc tgagggacct    300
ctaaggaaat cgcaggggag atgagacatg ttccggagg ctatgagatt gctcagatct    360
tcttctccac tggcctttgc ggtttggccc aatcgagtga gcctttacgg gtgttaagcc    420
```

```
tccgttctcc aacccagagc aaaggctggc agtgctgccc tcttgaccgc tgtcttgcag    480
gatctgatct ctgctcttga caccgcgggc tttaagggca ccagagcggg agagtcgtcc    540
gcgccaaaag gctgcgagcc tgactgctct tttttggagg atgccaggtt ccctctccta    600
caggactcaa tcccagtctg caacggaccc agtaccagca ctgtggcgtg aggtacgcac    660
actcagagtc ccccaaggtg tagaataagt ctttaaacag tcaaaaacag atattttaaa    720
acccagggaa ttctgctttg gttgagaaac agcgccttct gagagcgaag aactcattag    780
tttttagcgg tgatggcggg tgaactgtcc aaggcagaa tcgctctctc ctgtgtcatt     840
agtacatcag ctgaaaggca agcaaacagt tctttacgtc tgggaaaggg ctttaaggcc    900
cgctgcttgc gtgaagggca gatttgatgc agctataaac caggacatag acaggaacaa    960
aattcgggtt atttaagcaa aattctttag cagggaaagg gaggtgggaa ggagacggaa   1020
gggtgacgtc actgggggga gtggccacag tcttaagaaa agtcggcggg cctggggaga   1080
ccacaattgt gggacatagt ctcagc                                         1106
```

<210> SEQ ID NO 6
<211> LENGTH: 1030
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 6

```
cctgggagaa tggcccctgg cttcctcag ggatcttctg tgccgtgtat ccgctacccg      60
gggctgattt ctgtgctcca ctctctaggg cactctcctt ggatatagta ctgacctcct    120
gtgctcagtc cctggacgat cagtcccagt gtctgaaagg gtatccagga gttgaggagt    180
agggaacaac tgagggttgg taaaagtcgg agcctgaggg acctctaagg aaatggcagg    240
ggagatgaga catgttgcgg gaggctatga gattgctcag atcttcttct ccactggcct    300
ttgcggtttg gcccaatcga gtgagccttt acgggtgtta agcctccgtt ctccaaccca    360
gagcaaaggc tggcagtgct gccctcttga ccgctgtctt gcaggatctg atctctgctc    420
ttgacaccgc gggctttaag ggcaccagag cgggagagtc gtccgcgcca aaaggctgcg    480
agccagactg ctcttttttg gaggatgcca ggttccctct cctacaggac tcaatccctg    540
tctgcaacgg acccagtacc agcactgtgg cgtgaggtac gcacactcag agtcccccaa    600
ggtgtagaat aagtctttaa acagtcaaaa acagatattt taaacccag ggaattctgc     660 tttggttgag aaacagcgcc ttctgagagc gaagaactca ttagttttta gccgtgatgg    720
cgggtgaact gtcccaaggc agaatcgctc tctcctgtgt cattagtaca tcagctgaaa    780
ggcaagcaaa cagttctta cgtctgggaa agggctttaa ggcccgctgc ttgcgtgaag     840
gggagatttg atgcagctat aaaccaggac atagacagga acaaaattcg ggttatttaa    900
gcaaaattct ttagcaggga aagggaggtg ggaaggagac gaagggtga cgtcactggg     960 gggagtggcc acagtcttaa gaaaagtcgg cggggctggg gagaccacaa ttgtgggaca   1020
tagtctcagc                                                         1030
```

<210> SEQ ID NO 7
<211> LENGTH: 954
<212> TYPE: DNA
<213> ORGANISM: Artificial Sequence
<220> FEATURE:
<223> OTHER INFORMATION: Description of Artificial Sequence: Synthetic Sequence

<400> SEQUENCE: 7

| tccactctct | agggcactct | ccttggatat | agtactgacc | tcctgtgctc | actccctgga | 60 |
| cgatcagtcc | cagtgtctga | aagggtatcc | aggagttgag | gagtagggaa | caactgaggg | 120 |
| ttggtaaaag | tcggagcctg | agggacctct | aaggaaatgg | caggggagat | gagacatgtt | 180 |
| ccgggaggct | atgagattgc | tcacatcttc | ttctccactg | gcctttgcgg | tttggcccaa | 240 |
| tcgagtgagc | ctttacgggt | gttaagcctc | cgttctccaa | cccagagcaa | aggctggcag | 300 |
| tgctgccctc | ttgaccgctg | tcttgcagga | tctgatctct | gctcttgaca | ccgcgcgctt | 360 |
| taagggcacc | agagcgggag | agtcgtccgc | gccaaaaggc | tgcgagcctg | actgctcttt | 420 |
| tttggaggat | gccaggttcc | ctctcctaca | ggactcaatc | cctgtctgca | acggacccag | 480 |
| taccagcact | gtggcgtgag | gtacgcagac | tcagagtccc | ccaaggtgta | aataagtct | 540 |
| ttaaacagtc | aaaaacagat | attttaaaac | ccagggaatt | ctgctttggt | tgagaaacag | 600 |
| cgccttctga | gagcgaagaa | ctcattagtt | tttagcggtg | atggcgggtg | aactgtccct | 660 |
| aggcagaatc | gctctctcct | gtgtcattag | tacatcagct | gaaaggcaag | caaacagttc | 720 |
| tttacgtctg | ggaaagggct | taaggcccg | ctgcttgcgt | gaaggggaga | tttgatgcag | 780 |
| ctataaacca | ggacatagac | aggaacaaaa | tacgggttat | taagcaaaa | tctttagca | 840 |
| gggaaaggga | ggtgggaagg | agacggaagg | gtgacgtcac | tgggggagt | ggccacagtc | 900 |
| ttaagaaaag | tcgcgggc | tggggagacc | acaattgtgg | gacatagtct | cagc | 954 |

<210> SEQ ID NO 8
<211> LENGTH: 878
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 8

| ctgaaagggt | atccaggagt | tcaggagtag | ggaacaactg | agggttggta | aaagtcggag | 60 |
| cctgagggac | tctaaggaa | atggcagggg | agatgagtca | tgttccggga | ggctatgaga | 120 |
| ttgctcagat | cttcttctcc | actggccttt | gcggtttggc | ccaatcgagt | gaggctttac | 180 |
| gggtgttaag | cctccgttct | ccaacccaga | gcaaaggctg | gcagtgctgc | cctcttgacc | 240 |
| gctgtcttgg | aggatctgat | ctctgctctt | gacaccgcgg | gctttaaggg | caccagagcg | 300 |
| ggagagtcgt | ccgcgccaaa | aggctccgag | cctgactgct | cttttttgga | ggatgccagg | 360 |
| ttccctctcc | tacaggactc | aatccctgtc | tgcaacggac | cgagtaccag | cactgtggcg | 420 |
| tgaggtacgc | acactcagag | tcccccaagg | tgtagaataa | gtctttaaac | agtcaaaaac | 480 |
| agatatttta | aaacccaggg | aattctgctt | tggttgagaa | acagcgcctt | ctgagagcga | 540 |
| agaactcatt | agtatttagc | ggtgatggcg | ggtgaactgt | cccaaggcag | aatcgctctc | 600 |
| tcctgtgtca | ttagtacatc | agctgaaagg | caagcaaaca | gttctttacg | tctgggaaag | 660 |
| ggctttaagg | cccgctgctt | gcgtgaaggg | gagatttgat | gcagcaataa | accaggacat | 720 |
| agacaggaac | aaaattcggg | ttatttaagc | aaaattcttt | agcagggaaa | gggaggtggg | 780 |
| aaggagacgg | aagggtgacg | tcactggggg | gagtggccac | agtcttaaga | aaagtcggcg | 840 |
| gggctgggga | gaccacattt | gtgggacata | gtctcagc | | | 878 |

<210> SEQ ID NO 9

<211> LENGTH: 876
<212> TYPE: DNA
<213> ORGANISM: Artificial Sequence
<220> FEATURE:
<223> OTHER INFORMATION: Description of Artificial Sequence: Synthetic Sequence

<400> SEQUENCE: 9

| | | | | | |
|---|---|---|---|---|---|
| ctgaaagggt | atccaggagt | tcaggagtag | ggaacaactg | agggttggta | aaagtcggag | 60 |
| cctgagggac | ctctaaggaa | atggcagggg | agatgagtca | tgttccggga | ggctatgaga | 120 |
| ttgctcagat | cttcgtctcc | actggccttt | gcggtttggc | ccaatcgagt | gagggctttac | 180 |
| gggtgttaag | cctccgttct | ccaacccaga | gcaaaggctg | gcagtgctgc | cctcttgacg | 240 |
| ctgtcttgga | ggatctgatc | tctgctcttg | acaccgcggg | ctttaagggc | accagagcgg | 300 |
| gagagtcgtc | cgcgccaaaa | ggctgcgagc | ctgactgctc | ttttttggag | gatgccaggt | 360 |
| tccctctcct | acaggactca | atccctgtct | gcaacgacc | cagtaccagc | actgtggcgt | 420 |
| gaggtacgca | cactcagatg | tcccccaagg | tgtagaataa | gtctttaaac | atcaaaaaca | 480 |
| gatattttaa | aacccaggga | attctgcttt | ggttgagaaa | cagcgccttc | tgagagcgaa | 540 |
| gaactcatta | gttttagcg | gtgatggcgg | gtgaactgtc | ccaaggcaga | attcgctctc | 600 |
| tcctgtgtca | ttagtacatc | agctgaaagg | caagcaaaca | gttctttacg | tctgggaaag | 660 |
| ggctttaagg | cccgctgctt | cgtgaaggg | gagattgatg | cagctataaa | ccaggacata | 720 |
| gacaggaaca | aaattcgggt | tattaagcaa | aattctttag | cagggaaagg | gaggtgggaa | 780 |
| ggagacggaa | gggtgacgtc | actgggggga | gtggccacag | tcttaagaaa | agtcggcggg | 840 |
| gctggggaga | ccacaattgt | gggacatagt | ctcagc | | | 876 |

<210> SEQ ID NO 10
<211> LENGTH: 1096
<212> TYPE: DNA
<213> ORGANISM: Artificial Sequence
<220> FEATURE:
<223> OTHER INFORMATION: Description of Artificial Sequence: Synthetic Sequence

<400> SEQUENCE: 10

| | | | | | |
|---|---|---|---|---|---|
| acacaacctt | gttaagacta | tgttagcttc | cagcagagaa | aagcagctgt | aaagacacaa | 60 |
| attcaagaag | gaaaccctgg | gagaatggcc | cctggctttc | ctctgggatc | ttctgtgccg | 120 |
| tgtatccgct | acccggggcg | atttctgtgc | tccactgtct | agggcactct | ccttggatat | 180 |
| agtactgacc | tcctgtgctc | agtccctgga | cgatcagtcc | cagtgtctga | aagggtatcc | 240 |
| aggagttgag | gagtagggac | aactgagggt | tggtaaaagt | cggagcctga | gggacctcta | 300 |
| aggaaatcgc | agggagatg | agacatgttc | cgggaggcta | tgagattgct | cagatcttct | 360 |
| tctccactgg | cctttgcggt | ttggcccaat | cgagtgagcc | tttacgggtg | ttaagcctcc | 420 |
| gttctccaac | ccagagcaaa | ggctggcagt | gctgccctct | tgacgctgtc | ttgcaggatc | 480 |
| tgatctctgc | tcttgacacc | gcgggcttaa | gggcaccaga | gcgggagagt | cgtccgcgcc | 540 |
| aaaaggctgc | gagcctgact | gctctttttt | ggaggatgcc | aggttccctc | tcctacagga | 600 |
| ctcaatccca | gtctgcaacg | gacccagtac | cagcactgtg | gcgtgaggta | cgcacactca | 660 |
| gagtcccca | aggtgtagaa | taagtctta | aacagtcaaa | aacagatatt | taaacccag | 720 |
| ggaattctgc | tttggttgag | aaacagcgcc | ttctgagagc | gaagaactca | ttagttttta | 780 |
| gcggtgatgg | cgggtgaact | gtcccaaggc | agaatcgctc | tctcctgtgt | cattagtaca | 840 |
| tcagtgaaag | gcaagcaaac | agttctttac | gtctgggaaa | gggctttaag | gcccgctgct | 900 |

```
tgcgtgaagg gcagatttga tgcagctata aaccaggaca tagacagaac aaaattcggg     960
ttatttaagc aaaattcttt agcaggaaag ggaggtggga aggagacgga agggtgacgt    1020
cactgggggg agtggccaca gtcttaagaa aagtcggcgg gcctggggag accacaattg    1080
gggacatagt ctcagc                                                    1096
```

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 11

```
cgtcgcgctg cttcggtgtc acccactcac catctt                                36
```

<210> SEQ ID NO 12
<211> LENGTH: 43
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 12

```
cagcctcgga atgagctgcc acaactgctc cgaccccag gtc                         43
```

<210> SEQ ID NO 13
<211> LENGTH: 59
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 13

```
ttctgccagc tactcttcga catggagttc ttcgtgtggc acctgctgca ccacaaggt       59
```

<210> SEQ ID NO 14
<211> LENGTH: 76
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 14

```
cagactggag cccttcgggt ggtacggggg tgtggtgcac cacgacctgc atcactctca      60
ctttaactgc aacttc                                                      76
```

<210> SEQ ID NO 15
<211> LENGTH: 53
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 15

```
tccactcgta gggcactctc cttggatata gtactgacct cctgtgctca gtc             53
```

<210> SEQ ID NO 16
<211> LENGTH: 54

-continued

```
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 16
tccactctgt agggcactct ccttggatat agtactgacc tcctgtgctc agtc         54
```

CHOLESTEROL 25-HYDROXYLASE

The research described in this application was supported in part by NIH grant HL20948. The U.S. government may have rights in any patent issuing on this application.

INTRODUCTION

1. Field of the Invention

The field of this invention is cholesterol regulation.

2. Background

Oxysterols are formed by the hydroxylation of the side chain of cholesterol. This modification renders the sterol more hydrophilic and confers two important biological properties. First, the increased hydrophilicity enhances the ability of the oxysterol to cross membranes and thereby facilitates its movement between intracellular compartments, cells and tissues. Second, oxysterols delivered in ethanol to cultured cells, are potent regulators of the expression of genes involved in sterol and fatty acid metabolism (1,2).

The enhanced solubility of oxysterols is exploited by the body to maintain cholesterol homeostasis. In several tissues and cell types, including the brain, kidney, endothelium, and macrophages, cholesterol is converted into oxysterols that subsequently traverse the plasma membrane and are transported to the liver (3–5). In the liver, they are converted into bile acids by a newly described biosynthetic pathway (6). These bile acids are essential for normal lipid and fat-soluble vitamin metabolism (7).

Oxysterols are both positive and negative regulators of gene expression. As positive effectors, they bind to and activate the nuclear receptor LXR (8), which in turn increases transcription of the cholesterol 7α-hydroxylase gene (9). This activation stimulates the conversion of cholesterol into bile acids (10). Mutation of the LXR gene in mice causes a loss of 7α-hydroxylase gene induction and a buildup of cholesterol in the liver (11). As negative regulators, oxysterols suppress the cleavage of two transcription factors known as sterol regulatory element binding proteins-1 and -2 (SREBP-1 and -2) (12). These proteins are synthesized as inactive precursors in the membrane compartment of the cell. When intracellular cholesterol levels decline, SREBPs are cleaved to release amino-terminal fragments that migrate to the nucleus and activate the transcription of a network of genes involved in cholesterol synthesis and supply (12). This activation in turn restores intracellular cholesterol levels.

Several oxysterols occur naturally, including 25-hydroxycholesterol(cholest-5-ene- 3β,25-diol), 24-hydroxycholesterol(cholest-5-ene-3β,24-diol), and 27-hydroxycholesterol(cholest-5-ene-3β,27-diol) (13). Of these three oxysterols, 25-hydroxycholesterol is the most potent regulator of gene transcription when assayed in vitro (1,2,9,11). Hence, 25-hydroxycholesterol biosynthetic enzymes would provide attractive targets for therapeutic inhibitor development, i.e. novel hypocholesteremic agents: by blocking 25-hydroxycholesterol synthesis, SREBPs remain in their active forms and stimulate expression of the LDL receptor, which in turn extracts LDL from the plasma, lowering serum cholesterol.

SUMMARY OF THE INVENTION

The invention provides methods and compositions relating to cholesterol 25-hydroxylase polypeptides having cholesterol 25-hydroxylase-specific structure and activity, related polynucleotides and modulators of cholesterol 25-hydroxylase function and serum cholesterol. For example, the subject cholesterol 25-hydroxylase polypeptides and polynucleotides can be used to regulate cholesterol 25-hydroxylase activity, and hence serum cholesterol in a mammalian host. The polypeptides may be recombinantly produced from transformed host cells from the subject cholesterol 25-hydroxylase polypeptide encoding nucleic acids or purified from natural sources such as mammalian cells. The invention provides isolated cholesterol 25-hydroxylase hybridization probes and primers capable of specifically hybridizing with natural cholesterol 25-hydroxylase genes, cholesterol 25-hydroxylase-specific binding agents such as specific antibodies, agonists and antagonists, cholesterol 25-hydroxylase transcriptional regulators, and methods of making and using the subject compositions in diagnosis (e.g. genetic hybridization screens for cholesterol 25-hydroxylase transcripts), therapy (e.g. cholesterol 25-hydroxylase inhibitors to modulate serum cholesterol) and in the biopharmaceutical industry (e.g. as immunogens, reagents for isolating natural 25-hydroxylase genes and transcripts, reagents for screening chemical libraries for lead pharmacological agents, etc.).

DETAILED DESCRIPTION OF THE INVENTION

The nucleotide sequence of natural human and mouse genes encoding natural human and mouse cholesterol 25-hydroxylase polypeptides are shown as SEQ ID NOS:1 and 3, their natural transcript cDNAs are SEQ ID NO:1, nucleotides 1–1355 and SEQ ID NO:3, nucleotides 1173–2526, respectively, each with an additional 3' poly A tail, and their full translates are shown as SEQ ID NOS:2 and 4, respectively.

The cholesterol 25-hydroxylase polypeptides of the invention include fragments of SEQ ID NOS:2 and 4 having human cholesterol 25-hydroxylase-specific amino acid sequence, binding specificity and function. Preferred polypeptides comprise at least 10, preferably at least 15, more preferably at least 25, more preferably at least 35, most preferably at least 50 consecutive residues of SEQ ID NO:2, wherein such polypeptides and/or consecutive residues are not contained in any conceptual translate of murine ESTs AA289153 and AA285796, nor human ESTs AI081548, WO1328, and N45640. The subject domains provide cholesterol 25-hydroxylase domain specific activity or function, such as cholesterol 25-specific hydroxylase or hydroxylase inhibitory activity, SCAP (28) binding or binding inhibitory activity, and/or cholesterol 25-hydroxylase specific antibody binding or binding inhibitory activity.

Cholesterol 25-hydroxylase-specific activity or function may be determined by convenient in vitro, cell-based, or in vivo assays, e.g. binding assays. The term binding assay is used generically to encompass any assay, including in vitro, cell-cuture or animal-based assays (e.g. using gene therapy techniques or with transgenics), etc. where the molecular interaction of a cholesterol 25-hydroxylase polypeptide with a specific binding target is evaluated. The binding target may be a natural intracellular binding target such as a cholesterol 25-hydroxylase substrate, a cholesterol 25-hydroxylase regulating protein or other regulator that directly modulates cholesterol 25-hydroxylase activity or its localization; or non-natural binding target such as a specific immune protein such as an antibody, or an cholesterol 25-hydroxylase specific agent such as those identified in screening assays such as described below. Cholesterol 25-hydroxylase-binding specificity may be assayed by hydroxylase activity, hydroxylase activity inhibition (e.g. ability of the subject polypeptides to function as negative effectors in cholesterol 25-hydroxylase-expressing cells), by binding equilibrium constants (usually at least about $10^7$ $M^{-1}$, preferably at least about $10^8$ $M^{-1}$, more preferably at least about $10^9$ $M^{-1}$), by immunogenicity (e.g. ability to elicit cholesterol 25-hydroxylase specific antibody in a heterologous host such as a mouse, rat, goat or rabbit), etc.

In a particular embodiment, the subject polypeptides provide cholesterol 25-hydroxylase-specific antigens and/or immunogens, especially when coupled to carrier proteins. For example, the subject polypeptides are covalently coupled to keyhole limpet antigen (KLH) and the conjugate is emulsified in Freunds complete adjuvant. Laboratory rabbits are immunized according to conventional protocol and bled. The presence of cholesterol 25-hydroxylase-specific antibodies is assayed by solid phase immunosorbant assays using immobilized cholesterol 25-hydroxylase polypeptides of SEQ ID NOS:2 and 4, see, e.g. Table 1.

polypeptides may be covalently or noncovalently part of a larger complex, such as larger polypeptides and/or various conjugates, etc. The polypeptides may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides binding agents specific to the claimed cholesterol 25-hydroxylase polypeptides, including substrates, agonists, antagonists, natural intracellular binding targets, etc., methods of identifying and making such agents, and their use in diagnosis, therapy and pharmaceutical development. For example, specific binding agents are useful in a variety of diagnostic and therapeutic applications,

TABLE 1

Immunogenic cholesterol 25-hydroxylase polypeptides eliciting cholesterol 25-hydroxylase-specific rabbit polyclonal antibody: cholesterol 25-hydroxylase polypeptide-KLH conjugates immmunized per protocol described above.

| Cholesterol 25-hydroxylase Polypeptide Sequence | Immuno- genicity | Cholesterol 25-hydroxylase Polypeptide Sequence | Immuno- genicity |
|---|---|---|---|
| SEQ ID NO:2, res 1–10 | +++ | SEQ ID NO:4, res 1–24 | +++ |
| SEQ ID NO:2, res 6–15 | +++ | SEQ ID NO:4, res 21–30 | +++ |
| SEQ ID NO:2, res 10–20 | +++ | SEQ ID NO:4, res 31–40 | +++ |
| SEQ ID NO:2, res 60–70 | +++ | SEQ ID NO:4, res 85–109 | +++ |
| SEQ ID NO:2, res 62–71 | +++ | SEQ ID NO:4, res 105–115 | +++ |
| SEQ ID NO:2, res 67–76 | +++ | SEQ ID NO:4, res 110–120 | +++ |
| SEQ ID NO:2, res 72–85 | +++ | SEQ ID NO:4, res 135–144 | +++ |
| SEQ ID NO:2, res 81–90 | +++ | SEQ ID NO:4, res 140–150 | +++ |
| SEQ ID NO:2, res 85–95 | +++ | SEQ ID NO:4, res 145–155 | +++ |
| SEQ ID NO:2, res 90–115 | +++ | SEQ ID NO:4, res 152–163 | +++ |
| SEQ ID NO:2, res 116–122 | +++ | SEQ ID NO:4, res 161–170 | +++ |
| SEQ ID NO:2, res 120–128 | +++ | SEQ ID NO:4, res 168–177 | +++ |
| SEQ ID NO:2, res 124–132 | +++ | SEQ ID NO:4, res 177–186 | +++ |
| SEQ ID NO:2, res 130–140 | +++ | SEQ ID NO:4, res 184–196 | +++ |
| SEQ ID NO:2, res 135–152 | +++ | SEQ ID NO:4, res 193–206 | +++ |
| SEQ ID NO:2, res 144–155 | +++ | SEQ ID NO:4, res 205–211 | +++ |
| SEQ ID NO:2, res 154–163 | +++ | SEQ ID NO:4, res 209–218 | +++ |
| SEQ ID NO:2, res 165–174 | +++ | SEQ ID NO:4, res 215–224 | +++ |
| SEQ ID NO:2, res 174–184 | +++ | SEQ ID NO:4, res 221–229 | +++ |
| SEQ ID NO:2, res 183–195 | +++ | SEQ ID NO:4, res 225–236 | +++ |
| SEQ ID NO:2, res 193–206 | +++ | SEQ ID NO:4, res 230–241 | +++ |
| SEQ ID NO:2, res 205–211 | +++ | SEQ ID NO:4, res 236–246 | +++ |
| SEQ ID NO:2, res 215–224 | +++ | SEQ ID NO:4, res 240–249 | +++ |
| SEQ ID NO:2, res 225–236 | +++ | SEQ ID NO:4, res 247–256 | +++ |
| SEQ ID NO:2, res 236–246 | +++ | SEQ ID NO:4, res 251–260 | +++ |
| SEQ ID NO:2, res 247–256 | +++ | SEQ ID NO:4, res 255–265 | +++ |
| SEQ ID NO:2, res 255–265 | +++ | SEQ ID NO:4, res 260–272 | +++ |
| SEQ ID NO:2, res 260–272 | +++ | SEQ ID NO:4, res 267–298 | +++ |

The claimed cholesterol 25-hydroxylase polypeptides are isolated or pure: an "isolated" polypeptide is unaccompanied by at least some of the material with which it is associated in its natural state. Isolated polypeptides encompass cholesterol 25-hydroxylase polypeptides covalently joined to a non-natural or heterologous component, such as a non-natural amino acid or amino acid sequence or a natural amino acid or sequence other than that which the polypeptide is joined to in a natural protein, are preferably in solution, and preferably constitute at least about 0.5%, and more preferably at least about 5% by weight of the total polypeptide in a given sample and pure polypeptides constitute at least about 90%, and preferably at least about 99% by weight of the total polypeptide in a given sample. The especially where disease or disease prognosis is associated with unoptimized utilization of a pathway involving one or more of the subject polypeptides, e.g. cholesterol regulation. Novel cholesterol 25-hydroxylase-specific binding agents include cholesterol 25-hydroxylase-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as in vitro, cell-based and animal-based binding assays described herein, or otherwise known to those of skill in the art, etc.

Agents of particular interest modulate cholesterol 25-hydroxylase function, e.g. cholesterol 25-hydroxylase-dependent hydroxylation, and including dominant negative deletion mutants, etc. Accordingly, the invention also provides methods for modulating cholesterol regulation in a cell comprising the step of modulating cholesterol 25-hydroxylase activity, e.g. by contacting the cell with a substrate, agonist or antagonist of a resident cholesterol 25-hydroxylase, a dominant negative cholesterol 25-hydroxylase deletion mutant, or cholesterol 25-hydroxylase polynucleotide (below).

The amino acid sequences of the disclosed cholesterol 25-hydroxylase polypeptides are used to back-translate cholesterol 25-hydroxylase polypeptide-encoding polynucleotides optimized for selected expression systems (Holler et al. (1993) Gene 136, 323–328; Martin et al. (1995) Gene 154, 150–166) or used to generate degenerate primers and probes for use in the isolation of natural cholesterol 25-hydroxylase-encoding nucleic acid sequences (see, e.g. "GCG" software, Genetics Computer Group, Inc, Madison Wis.). The terms polynucleotide and nucleic acid are used interchangeably to refer to any polymer of nucleotides, without restriction by length. Cholesterol 25-hydroxylase-encoding polynucleotides may be used in cholesterol 25-hydroxylase-expression vectors and incorporated into recombinant host cells, e.g. for expression and screening, transgenic animals, e.g. for functional studies such as the efficacy of candidate drugs for disease associated with cholesterol 25-hydroxylase-modulated cell function, etc.

The invention also provides polynucleotides, e.g. hybridization probes and replication/amplification primers, comprising a cholesterol 25-hydroxylase cDNA specific sequence comprising at least one of SEQ ID NO:1 or 3 and polynucleotides comprising a nucleotide sequence sufficient to effect specific hybridization to SEQ ID NO:1 or 3 and not contained in any of murine ESTs AA289153 and AA285796, nor human ESTs A1081548, WO1328, and N456401, such specifically hybridizing polynucleotides including polynucleotides comprising one or more fragments of SEQ ID NO:1 or 3. Such polynucleotides and fragments are at least 12, preferably at least 24, more preferably at least 48, more preferably at least 96 and most preferably at least 182 nucleotides in length. Demonstrating specific hybridization generally requires stringent conditions, for example, hybridizing in a buffer comprising 30% formamide in 5×SSPE (0.18 M NaCl, 0.01 M $NaPO_4$, pH 7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. Specifically hybridizing polynucleotides are readily identified in convenient gel-based assays; for example, polynucleotides comprising SEQ ID NOS:5–10 are shown to specifically hybridize with SEQ ID NO:1 and/or 3 under the foregoing preferred hybridization conditions. Cholesterol 25-hydroxylase nucleic acids can also be distinguished using alignment algorithms, e.g. nucleic acids having a BLASTn 2.0 (See, http://www.ncbi.nlm.nih.gov/BLAST/) bit score of at least 100, preferably at least 200 more preferably at least 400, most preferably at least 800 with a significance of at least e-50, preferably at least e-75, more preferably at least e-100, most preferably at least e-125, using default program settings.

TABLE 2

Exemplary cholesterol 25-hydroxylase nucleic acids which hybridize with a strand of at least one of SEQ ID NO:1 and 3 under Conditions I and II.

| SEQ ID NO:1-Specific Cholesterol 25-hydroxylase Polynucleotides | Specific Hybrids | SEQ ID NO:3-Specific Cholesterol 25-hydroxylase Polynucleotides | Specific Hybrids |
|---|---|---|---|
| SEQ ID NO:1, nucl 1–36 | + | SEQ ID NO:3, nucl 1–32 | + |
| SEQ ID NO:1, nucl 32–68 | + | SEQ ID NO:3, nucl 40–70 | + |
| SEQ ID NO:1, nucl 207–230 | + | SEQ ID NO:3, nucl 98–124 | + |
| SEQ ID NO:1, nucl 248–282 | + | SEQ ID NO:3, nucl 148–182 | + |
| SEQ ID NO:1, nucl 344–376 | + | SEQ ID NO:3, nucl 222–256 | + |
| SEQ ID NO:1, nucl 352–386 | + | SEQ ID NO:3, nucl 258–286 | + |
| SEQ ID NO:1, nucl 388–424 | + | SEQ ID NO:3, nucl 304–327 | + |
| SEQ ID NO:1, nucl 406–431 | + | SEQ ID NO:3, nucl 381–416 | + |
| SEQ ID NO:1, nucl 420–446 | + | SEQ ID NO:3, nucl 468–499 | + |
| SEQ ID NO:1, nucl 438–469 | + | SEQ ID NO:3, nucl 556–583 | + |
| SEQ ID NO:1, nucl 466–500 | + | SEQ ID NO:3, nucl 607–635 | + |
| SEQ ID NO:1, nucl 488–522 | + | SEQ ID NO:3, nucl 685–717 | + |
| SEQ ID NO:1, nucl 502–532 | + | SEQ ID NO:3, nucl 745–775 | + |
| SEQ ID NO:1, nucl 530–570 | + | SEQ ID NO:3, nucl 823–854 | + |
| SEQ ID NO:1, nucl 544–568 | + | SEQ ID NO:3, nucl 895–922 | + |
| SEQ ID NO:1, nucl 551–578 | + | SEQ ID NO:3, nucl 978–1003 | + |
| SEQ ID NO:1, nucl 565–592 | + | SEQ ID NO:3, nucl 1049–1082 | + |
| SEQ ID NO:1, nucl 578–603 | + | SEQ ID NO:3, nucl 1138–1165 | + |
| SEQ ID NO:1, nucl 589–612 | + | SEQ ID NO:3, nucl 1245–1276 | + |
| SEQ ID NO:1, nucl 600–624 | + | SEQ ID NO:3, nucl 1280–1312 | + |
| SEQ ID NO:1, nucl 607–638 | + | SEQ ID NO:3, nucl 1495–1522 | + |
| SEQ ID NO:1, nucl 630–660 | + | SEQ ID NO:3, nucl 1602–1628 | + |
| SEQ ID NO:1, nucl 645–669 | + | SEQ ID NO:3, nucl 1686–1716 | + |
| SEQ ID NO:1, nucl 655–680 | + | SEQ ID NO:3, nucl 1788–1812 | + |
| SEQ ID NO:1, nucl 662–688 | + | SEQ ID NO:3, nucl 1824–1856 | + |
| SEQ ID NO:1, nucl 684–716 | + | SEQ ID NO:3, nucl 1922–1952 | + |
| SEQ ID NO:1, nucl 692–722 | + | SEQ ID NO:3, nucl 1965–1990 | + |

TABLE 2-continued Exemplary cholesterol 25-hydroxylase nucleic acids which
hybridize with a strand of at least one of SEQ ID NO:1 and 3
under Conditions I and II.

| SEQ ID NO:1-Specific Cholesterol 25-hydroxylase Polynucleotides | Specific Hybrids | SEQ ID NO:3-Specific Cholesterol 25-hydroxylase Polynucleotides | Specific Hybrids |
|---|---|---|---|
| SEQ ID NO:1, nucl 718–744 | + | SEQ ID NO:3, nucl 2130–2155 | + |
| SEQ ID NO:1, nucl 725–751 | + | SEQ ID NO:3, nucl 2402–2425 | + |
| SEQ ID NO:1, nucl 745–772 | + | SEQ ID NO:3, nucl 2518–2544 | + |
| SEQ ID NO:1, nucl 760–784 | + | SEQ ID NO:3, nucl 2645–2672 | + |
| SEQ ID NO:1, nucl 778–803 | + | SEQ ID NO:3, nucl 2760–2784 | + |
| SEQ ID NO:1, nucl 1352–1378 | + | SEQ ID NO:3, nucl 2852–2878 | + |
| SEQ ID NO:1, nucl 1380–1406 | + | SEQ ID NO:3, nucl 2921–2951 | + |

The invention also provides regulators of cholesterol 25-hydroxylase gene expression, including natural upstream (5') cholesterol 25-hydroxylase gene transcriptional regulatory elements. Native cholesterol 25-hydroxylase promoter elements may be truncated and recombined to generate novel cholesterol 25-hydroxylase transcriptional regulatory elements. In a particular embodiment, the invention provides promoters comprising a cholesterol 25-hydroxylase gene specific sequence comprising SEQ ID NO:3, nucleotides 1–1182 and promoters comprising a nucleotide sequence that effects specific hybridization to SEQ ID NO:3, nucleotides 1–1182, provides one or more cholesterol 25-hydroxylase promoter activities and comprises one or more fragments of SEQ ID NO:3, nucleotides 1–1182. Specifically hybridizing polynucleotides are readily identified in convenient gel-based assays; for example, polynucleotides comprising SEQ ID NOS:11–16 are shown to specifically hybridize with SEQ ID NO:3, nucleotides 1–1182 under the foregoing preferred hybridization conditions. Such polynucleotides and fragments are at least 12, preferably at least 24, more preferably at least 48, more preferably at least 96, and most preferably at least 182 nucleotides in length. Generally, such elements comprise one or more cholesterol 25-hydroxylase promoter DNA binding protein and/or transcription factor binding sites, examples of which are provided in Table 3.

TABLE 3

Cholesterol 25-hydroxylase promoter DNA binding protein (BP)
and/or transcription factor (TF) binding sites.

| Cholesterol 25-Hydroxylase Promoter Binding Sites | DNA BP/TF | Cholesterol 25-Hydroxylase Promoter Binding Sites | DNA BP/TF |
|---|---|---|---|
| SEQ ID NO:3, nucl 1–8 | MZF1 | SEQ ID NO:3, nucl 813–823 | CP2 |
| SEQ ID NO:3, nucl 1–10 | SP1 | SEQ ID NO:3, nucl 823–828 | SRY |
| SEQ ID NO:3, nucl 12–19 | MZF1 | SEQ ID NO:3, nucl 847–859 | Oct-1 |
| SEQ ID NO:3, nucl 47–58 | HNF-3b | SEQ ID NO:3, nucl 851–857 | CdxA |
| SEQ ID NO:3, nucl 53–59 | SRY | SEQ ID NO:3, nucl 853–859 | SRY |
| SEQ ID NO:3, nucl 55–67 | C/EBP | SEQ ID NO:3, nucl 865–874 | GATA-1 |
| SEQ ID NO:3, nucl 64–70 | CdxA | SEQ ID NO:3, nucl 865–874 | GATA-2 |
| SEQ ID NO:3, nucl 75–81 | SRY | SEQ ID NO:3, nucl 909–921 | Oct-1 |
| SEQ ID NO:3, nucl 95–106 | HNF3b | SEQ ID NO:3, nucl 913–919 | CdxA |
| SEQ ID NO:3, nucl 133–139 | CdxA | SEQ ID NO:3, nucl 936–942 | SRY |
| SEQ ID NO:3, nucl 197–206 | GATA-2 | SEQ ID NO:3, nucl 936–947 | HNF-3b |
| SEQ ID NO:3, nucl 215–224 | GATA-1 | SEQ ID NO:3, nucl 945–951 | SRY |
| SEQ ID NO:3, nucl 219–225 | CdxA | SEQ ID NO:3, nucl 948–954 | CdxA |
| SEQ ID NO:3, nucl 265–274 | c-Ets | SEQ ID NO:3, nucl 954–965 | Ik-2 |
| SEQ ID NO:3, nucl 311–320 | GATA-2 | SEQ ID NO:3, nucl 955–963 | Lyf-1 |
| SEQ ID NO:3, nucl 388–395 | MZF1 | SEQ ID NO:3, nucl 967–973 | CdxA |
| SEQ ID NO:3, nucl 407–415 | STATx | SEQ ID NO:3, nucl 989–996 | MZF1 |
| SEQ ID NO:3, nucl 420–429 | GATA-2 | SEQ ID NO:3, nucl 1010–1016 | CdxA |
| SEQ ID NO:3, nucl 459–466 | E2F | SEQ ID NO:3, nucl 1046–1059 | C/EBPa |
| SEQ ID NO:3, nucl 464–472 | GATA-3 | SEQ ID NO:3, nucl 1046–1059 | C/EBPb |
| SEQ ID NO:3, nucl 464–473 | GATA-1 | SEQ ID NO:3, nucl 1047–1053 | CdxA |
| SEQ ID NO:3, nucl 479–485 | CdxA | SEQ ID NO:3, nucl 1051–1057 | SRY |
| SEQ ID NO:3, nucl 586–592 | CdxA | SEQ ID NO:3, nucl 1096–1107 | CREB |
| SEQ ID NO:3, nucl 617–624 | E2F | SEQ ID NO:3, nucl 1100–1107 | CREB |
| SEQ ID NO:3, nucl 648–656 | Lyf-1 | SEQ ID NO:3, nucl 1100–1107 | CRE-BP |
| SEQ ID NO:3, nucl 680–693 | p300 | SEQ ID NO:3, nucl 1100–1111 | CREB |
| SEQ ID NO:3, nucl 695–703 | v-Myb | SEQ ID NO:3, nucl 1109–1117 | MZF1 |
| SEQ ID NO:3, nucl 745–752 | MZF1 | SEQ ID NO:3, nucl 1126–1139 | C/EBPb |
| SEQ ID NO:3, nucl 749–759 | deltaE | SEQ ID NO:3, nucl 1132–1141 | HSF2 |
| SEQ ID NO:3, nucl 757–763 | CdxA | SEQ ID NO:3, nucl 1132–1141 | HSF1 |
| SEQ ID NO:3, nucl 781–787 | SRY | SEQ ID NO:3, nucl 1144–1153 | Sp1 |
| SEQ ID NO:3, nucl 805–811 | CdxA | SEQ ID NO:3, nucl 1147–1154 | MZF1 |
| SEQ ID NO:3, nucl 813–819 | SRY | | |

Transcriptional regulatory activity is conveniently assayed in transcriptional reporter assays. For example, Table 4 provides cholesterol 25-hydroxylase gene promoter constructs which can regulate expression of luciferase enzymatic activity in $CaPO_4$ transfected 293 or HeLa cells. For these assays, cells are harvested 18 hrs post transfection and assayed for luciferase.

TABLE 4

Active Cholesterol 25-hydroxylase promoter constructs.

| SEQ ID NO:3-Specific Cholesterol 25-hydroxylase Promoter Constructs | Luciferase Expression |
|---|---|
| SEQ ID NO:3, nucl 1–1182 | ++++ |
| SEQ ID NO:3, nucl 12–1182 | ++++ |
| SEQ ID NO:3, nucl 64–1182 | ++++ |
| SEQ ID NO:3, nucl 197–1182 | ++++ |
| SEQ ID NO:3, nucl 222–1182 | ++++ |
| SEQ ID NO:3, nucl 388–1182 | ++++ |
| SEQ ID NO:3, nucl 464–1182 | ++++ |
| SEQ ID NO:3, nucl 586–1182 | ++++ |
| SEQ ID NO:3, nucl 695–1182 | ++++ |
| SEQ ID NO:3, nucl 757–1182 | ++++ |
| SEQ ID NO:3, nucl 1–320 & 813–1182 | ++++ |
| SEQ ID NO:3, nucl 1–485 & 853–1182 | ++++ |
| SEQ ID NO:3, nucl 1–693 & 909–1182 | ++++ |
| SEQ ID NO:3, nucl 1–1172 | ++++ |
| SEQ ID NO:3, nucl 12–1172 | ++++ |
| SEQ ID NO:3, nucl 64–1172 | ++++ |
| SEQ ID NO:3, nucl 197–1172 | ++++ |
| SEQ ID NO:3, nucl 222–1172 | ++++ |
| SEQ ID NO:3, nucl 388–1172 | ++++ |
| SEQ ID NO:3, nucl 464–1172 | ++++ |
| SEQ ID NO:3, nucl 586–1172 | ++++ |
| SEQ ID NO:3, nucl 695–1172 | ++++ |
| SEQ ID NO:3, nucl 757–1172 | ++++ |
| SEQ ID NO:3, nucl 1–320 & 813–1172 | ++++ |
| SEQ ID NO:3, nucl 1–485 & 853–1172 | ++++ |
| SEQ ID NO:3, nucl 1–693 & 909–1172 | ++++ |

The subject polynucleotides are of synthetic/non-natural sequences and/or are isolated, i.e. unaccompanied by at least some of the material with which it is associated in its natural state, preferably constituting at least about 0.5%, preferably at least about 5% by weight of total polynucleotides present in a given fraction, and usually recombinant, meaning they comprise a non-natural sequence or a natural sequence joined to nucleotide(s) other than that to which it is joined on a natural chromosome. Recombinant polynucleotides comprising the nucleotide sequence of SEQ ID NO:1 or 3, or fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that to which it is joined on a natural chromosome. While the polynucleotides are usually RNA or DNA, it is often advantageous to use polynucleotides comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of cholesterol 25-hydroxylase genes and gene transcripts and in detecting or amplifying nucleic acids encoding additional cholesterol 25-hydroxylase homologs and structural analogs. In diagnosis, cholesterol 25-hydroxylase hybridization probes find use in identifying wild-type and mutant cholesterol 25-hydroxylase alleles in clinical and laboratory samples. Mutant alleles are used to generate allele-specific oligonucleotide (ASO) probes for high-throughput clinical diagnoses. In therapy, therapeutic cholesterol 25-hydroxylase nucleic acids are used to modulate cellular expression or intracellular concentration or availability of active cholesterol 25-hydroxylase.

For example, cholesterol 25-hydroxylase nucleic acids are used to modulate cellular expression or intracellular concentration or availability of active cholesterol 25-hydroxylase protein. Cholesterol 25-hydroxylase inhibitory nucleic acids are typically antisense: single-stranded sequences comprising complements of the disclosed natural cholesterol 25-hydroxylase transcript sequences. Antisense modulation of the expression of a given cholesterol 25-hydroxylase protein may employ antisense nucleic acids operably linked to gene regulatory sequences. Cell are transfected with a vector comprising a cholesterol 25-hydroxylase sequence with a promoter sequence oriented such that transcription of the gene yields an antisense transcript capable of binding to endogenous cholesterol 25-hydroxylase encoding mRNA. Alternatively, single-stranded antisense nucleic acids that bind to genomic DNA or mRNA encoding cholesterol 25-hydroxylase protein may be administered to the target cell, in or temporarily isolated from a host, at a concentration that results in a substantial reduction in expression of the targeted protein. An enhancement in cholesterol 25-hydroxylase expression is effected by introducing into the targeted cell type cholesterol 25-hydroxylase nucleic acids that increase the functional expression of the corresponding gene products. Such nucleic acids may be cholesterol 25-hydroxylase expression vectors, vectors that upregulate the functional expression of an endogenous allele, or replacement vectors for targeted modification of endogenous mutant or wild type alleles. Techniques for introducing the nucleic acids into viable cells are known in the art and include retroviral-based transfection, viral coat protein-liposome mediated transfection, etc.

The invention provides efficient methods of identifying agents, compounds or lead compounds for agents active at the level of a cholesterol 25-hydroxylase modulatable cellular function and/or cholesterol 25-hydroxylase gene expression, including transcription. A wide variety of assays for transcriptional modulators or binding agents are provided including labeled in vitro ligand binding or hydroxylation assays, immunoassays, cell-based reporter assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

A wide variety of assays for cholesterol 25-hydroxylase transcriptional regulators are provided including cell-based transcription reporter assays, gel-based or solid-phase promoter-protein binding assays, etc. In a particular embodiment, cholesterol 25-hydroxylase promoter-luciferase reporter constructs are used to transfect cells such as HeLa cells for cell-based transcription assays. Specifically, HeLa cells are plated onto microtiter plates and used to screen libraries of candidate agents for lead compounds that modulate the transcriptional regulation of the cholesterol 25-hydroxylase gene promoter, as monitored by luciferase expression.

A wide variety of assays for binding agents, i.e. screens for compounds that modulate cholesterol 25-hydroxylase interaction with a natural cholesterol 25-hydroxylase binding target are also provides. These assays employ a mixture of components including a cholesterol 25-hydroxylase polypeptide, which may be part of a fusion product with another polypeptide, e.g. a peptide tag for detection or anchoring, etc. The assay mixtures comprise a natural intracellular cholesterol 25-hydroxylase binding target. In a particular embodiment, the binding target is a cholesterol 25-hydroxylase substrate, agonist, antagonist or regulator. In the case of polypeptide regulators, one may use portions (e.g. peptides) thereof so long as the portion provides binding affinity and avidity to the subject cholesterol 25-hydroxylase polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like, salts, buffers, neutral proteins, e.g. albumin, detergents, protease inhibitors, nuclease inhibitors, antimicrobial agents, etc. may be used. In a preferred embodiment, the mixture is provided as a cell line expressing the cholesterol 25-hydroxylase polypeptide in a regulated fashion, as the TR3202a cells described below, or in a cell extract, wherein cholesterol 25-hydroxylase expression is induced and radiolabeled cholesterol substrate is added to the cells.

The resultant mixture is incubated under conditions whereby, but for the presence of the candidate pharmacological agent, the cholesterol 25-hydroxylase polypeptide specifically binds the cellular binding target, portion or analog with a reference binding affinity. The mixture components can be added in any order that provides for the requisite bindings, and incubations may be performed at any temperature which facilitates optimal binding. Incubation periods are likewise selected for optimal binding but also minimized to facilitate rapid, high-throughput screening. In a preferred embodiment, the binding effects the conversion of the radiolabeled substrate to 25-hydroxycholesterol.

After incubation, the agent-biased binding between the cholesterol 25-hydroxylase polypeptide and one or more binding targets is detected by any convenient way. A variety of methods may be used to detect the change depending on the nature of the product and other assay components, e.g. through optical or electron density, radiative emissions, nonradiative energy transfers, etc. or indirectly detected with antibody conjugates, etc. For the preferred cell- or extract-based cholesterol 25-hydroxylase assays, 'binding' is generally detected by a change in the hydroxylation of a cholesterol 25-hydroxylase substrate, such as the conversion of radiolabeled cholesterol to 25 hydroxycholesterol, e.g. by thin layer chromatography.

A difference in the binding affinity of the cholesterol 25-hydroxylase to the target in the absence of the agent as compared with the binding affinity in the presence of the agent indicates that the agent modulates the binding of the cholesterol 25-hydroxylase to the cholesterol 25-hydroxylase binding target. Analogously, in the cell-based assay also described below, a difference in cholesterol 25-hydroxylase-dependent transcriptional activation in the presence and absence of an agent indicates the agent modulates cholesterol 25-hydroxylase function. A difference, as used herein, is statistically significant and preferably represents at least a 50%, more preferably at least a 90% difference.

The following experimental section and examples are offered by way of illustration and not by way of limitation.

EXAMPLES

EXPERIMENTAL PROCEDURES

Abbreviations—cholesterol, 5-cholesten-3β-ol; 25-hydroxycholesterol, cholest-5-ene-3β,25-diol; 24-hydroxycholesterol, cholest-5-ene-3β,24-diol; 27-hydroxycholesterol, cholest-5-ene-3β,27-diol; cholestanol, 5α-cholestan-3β-ol; epicholesterol, 5-cholesten-3α-ol; coprostanol, 5β-cholestan-3β-ol; desmosterol, 5,24-cholestadien-3β-ol; sitosterol, 5-cholesten-24β-ethyl-3β-ol; 25-oxo-27-noncholesterol, 2,7-nor-25-oxo-5-choleste 3β-ol.

Expression Cloning—Total RNA was prepared from 400 mg of an SREBP-1a transgenic mouse liver (14) using RNA-Stat 60 (Tel-Test, Inc. Friendswood, Tex.). Poly(A)$^+$ RNA was prepared from total RNA by two cycles of chromatography on oligo(dT) (mRNA Purification Kit, Pharmacia, Piscataway, N.J.). A size-fractionated, directional cDNA library with SalI and NotI cohesive ends at the 5'- and 3'-termini, respectively, was constructed from 4 μg of poly(A)$^+$ RNA using a Superscript Plasmid Kit (Life Technologies, Gaithersburg, Md.). Size-fractionated cDNA (>1.0 kb, 10 ng) was ligated with 50 ng of pCMV6 expression vector (a derivative of pCMV4 (15) containing a NotI site in the polylinker) using a protocol and reagents supplied with the Superscript kit. Prior to ligation, the pCMV6 vector (1.2 μg) was digested for 2 h with 10 units of NotI and SalI, respectively, in 30 μl of 1×SalI restriction buffer (New England Biolabs, Beverly, Mass.). The digested plasmid was purified by phenol:chloroform (1:1, v/v) extraction, electrophoresed on a 0.8% agarose gel, and recovered from the gel using a QIAquick Gel Extraction Kit (Qiagen GmbH, Germany).

Plasmid DNA was purified from the ligation reaction by precipitation with ammonium acetate-ethanol and resuspended in 4 μl of water, of which 1 μl was used to transform 40 μl of Electromax E. coli DH10B cells (Life Technologies). The transformed bacteria were diluted into 1000 ml of LB medium containing ampicillin. Aliquots of cells were plated on LB ampicillin plates for calculation of the total number of recombinants. The remainder was divided into 400 pools of 2.5-ml each that were grown to saturation overnight at 37° C. The total number of independent recombinants in the cDNA library was $1.5 \times 10^6$, and each pool contained an average of 3800 recombinants. DNA was prepared from individual pools using a Wizard Miniprep Kit (Promega Inc, Madison, Wis.). The yield of plasmid DNA from each pool was approximately 25 μg.

Human embryonic kidney 293 cells (ATCC # CRL 1573) were plated on day 0 at a density of $7 \times 10^5$ cells/60 mm dish in Medium A (Dulbecco's modified Eagle's medium (DMEM) containing 10% fetal calf serum, 100 u/ml penicillin, and 100 μg/ml streptomycin sulfate). On day 1, individual dishes were transfected with a mixture of plasmid DNAs that included pool DNA (5 μg), pCMV-StAR (2 μg), phct1 (2 μg), and pVA-1 (1 μg). The expression plasmid pCMV-StAR contains a full-length cDNA encoding the murine steroidogenic acute regulatory protein (StAR, ref. 16). The expression plasmid phct1 contains a full-length cDNA encoding the murine oxysterol 7α-hydroxylase enzyme (17,18). The plasmid pVA1 contains the adenovirus type 5 VAI gene (19). A positive control, in which cells were transfected with 1 ng of a murine sterol 27-hydroxylase expression plasmid diluted into 5 μg of pCMV6 vector alone, was included in every experiment. Aliquots (40 μl) of the transfection lipid pfx-8 (Invitrogen, Carlsbad, Calif.) dissolved in DMEM containing 15 μM HEPES were added to each plasmid mixture. Cells were incubated with the resulting lipid-DNA mixture in 5 ml of DMEM for 4 h at 37° C., in an atmosphere of 8.8% $CO_2$. Assay of cholesterol 25-hydroxylase activity was thereafter carried out as described below.

To subdivide the positive pool containing a cholesterol 25-hydroxylase cDNA, an aliquot (40 μl) of Electromax DH10B cells were transformed with 0.5 ng of DNA from the positive primary pool. A portion (0.5%) of the transformation mixture was diluted into 50 ml of LB medium containing ampicillin and divided into 20 pools, each containing ~490 recombinants for secondary screening. DNA was prepared from individual pools and 293 cells were transfected as above, except that 6-well plates were used in place of 60 mm dishes, and amounts of reagents were scaled down accordingly. Tertiary screening was similarly performed except subpools of 50 recombinants were transfected. Quaternary screening was carried out with pools of 10 cDNA isolates derived from a matrix array of individual cDNAs to identify a single cholesterol 25-hydroxylase cDNA.

Measurement of cholesterol 25-hydroxylase activity in whole cells—The transfection medium containing the cationic lipid was aspirated and replaced with 3 ml of Medium B (DMEM containing 10% newborn calf lipoprotein-poor serum, 100 u/ml penicillin, and 100 μg/ml streptomycin sulfate) supplemented with 5 μl of [4-$^{14}$C]cholesterol (56.6 mCi/mmol; 0.040 μCi/μl; New England Nuclear, Boston, Mass.). Cells were incubated for a further 60 h at 37° C. in an atmosphere of 8.8% $CO_2$.

Media from the transfected cells were collected and extracted with 8 ml of chloroform:methanol (2:1, v/v). The organic phase from each sample was taken to dryness under a stream of nitrogen and residues were dissolved in 40 μl aliquots of chloroform:methanol (2:1, v/v) and applied to 20×20 cm prescored LK5DF silica gel TLC plates (Whatman, Hillsboro, Oreg.) with preadsorbent layers. The plates were developed in ethyl acetate:toluene (4:6, v/v), and exposed to a Fuji BAS-MP phosphoimager plate overnight. Phosphoimage analysis was then performed on a Fuji BAS 1000 apparatus.

Isolation of Human Cholesterol 25-Hydroxylase cDNA—A 372 base pair (bp) expressed sequence tag (EST, GenBank #45640) with high sequence identity to a portion of the murine 25-hydroxylase cDNA was identified by BLAST search. A bacterial stab transformed with a plasmid containing the EST sequence cloned into the pT3T7 vector was obtained from Research Genetics, Inc, Huntsville, Ala. Plasmid DNA was prepared and a 245 bp fragment was amplified by the polymerase chain reaction. The thermocycler program consisted of 35 cycles of 94° C./30 sec; 60° C./30 sec; 72° C./30 sec. The amplified cDNA fragment was cloned into pGEM-T Easy (Promega Corp., Madison, Wis.). The insert was excised from the plasmid with EcoRI and used for the preparation of a radiolabeled probe by random octamer priming (Megaprime Labeling Kit, Amersham, Arlington Heights, Ill.). The probe was used to screen 200,000 plaques of a human lung cDNA library in bacteriophage λ gt10 (Cat # HL3004a, Clontech, Palo Alto, Calif.) using standard hybridization procedures (20). One positive clone was isolated whose cDNA insert was subcloned into the EcoRI sites of pBluescript SK$^+$ (Stratagene Corp., La Jolla, Calif.) and pCMV6, yielding plasmids pBS-h25 and pCMV-h25, respectively.

Gene Mapping—Cholesterol 25-hydroxylase gene sequences were isolated from a murine genomic library prepared from 129SvEv DNA and a human genomic library (Cat. #946204, Stratagene), both in bacteriophage λ FIX II, by screening with full-length cDNA probes corresponding to the murine and human cholesterol 25-hydroxylase cDNAs, respectively, using standard protocols (20). Approximately 600,000 murine and 400,000 human recombinants were screened and one positive clone from each library was identified and purified to homogeneity. The corresponding genomic DNA inserts were excised from the bacteriophage vectors and ligated into the NotI site of pBluescript SK$^+$, yielding plasmids pBS-mg25 and pBS-hg25, respectively.

The chromosomal location of the human cholesterol 25-hydroxylase gene was determined by fluorescent in situ hybridization (FISH) and by polymerase chain reaction amplification of somatic cell and radiation hybrid panel DNAs. FISH mapping was performed by See DNA Biotech, Inc. (Downsview, Ontario, Canada). The bacteriophage λ clone harboring the human 25-hydroxylase gene described above was labeled with biotinylated dATP for use as a FISH probe. Of 100 mitotic figures analyzed, 91 showed hybridization signals on paired sister chromatids corresponding to chromosome 10. Comparison of the signal positions with bands generated by staining with DAPI indicated that hybridization occurred at band q23. Radiation and somatic cell hybrid mapping was performed using DNAs in the Somatic Cell Hybrid Mapping Panel #2 (Coriell Institute of Medical Research, Camden, N.J.) and the Stanford G-3 radiation hybrid panel (Research Genetics, Huntsville, Ala.). The primer pair used for amplification correspond to nucleotides 79–98 and 333–314 of the human gene sequence. The thermocycler program consisted of 35 cycles of 94° C./15 sec; 68° C./30 sec on a Perkin Elmer GeneAmp 9600 machine. Only somatic cell hybrid DNAs containing human chromosome 10 produced a positive amplification signal. Analysis of the radiation hybrid data through the Stanford Genome Center server (rhserver@shgc.stanford.edu) indicated linkage of the cholesterol 25-hydroxylase gene to the SHGC-15188 marker (LOD score =4.4, cR_1000=45.76) on chromosome 10 in the vicinity of band q23.

DNA sequencing and RNA Blotting—DNA sequencing was performed on an ABI Prism 377 sequencer using thermocycler sequencing protocols and fluorescent dye terminators. Contiguous DNA sequences were assembled using MacVector software (IBI-Kodak Corp., New haven, Conn.) and sequence alignments were generated using a Lasergene software package (DNASTAR, Inc., Madison, Wis.).

For RNA blotting, a murine multiple tissue RNA blot (Clontech, #7762-1) was hybridized overnight in 50% formamide hybridization buffer at 42° C. with a full-length murine 25-hydroxylase cDNA probe using standard procedures (20). The probe was radioactively labeled by random nonamer priming with [$^{32}$P]CTP. The blot was washed stringently at 65° C., in 0.1×SSC containing 0.1% (w/v) SDS before exposure for 5 days to Kodak X-OMAT AR film at −80° C. using an intensifying screen.

Antibodies—An antipeptide antibody against the sequence corresponding to amino acids 69–83 of the murine cholesterol 25-hydroxylase was raised in rabbits. This sequence was synthesized as a multiple antigen peptide by Bio-Synthesis, Inc. (Lewisville, Tex.). For the initial immunization, 100 μg of peptide was administered intramuscularly as a dispersion in Freund's complete adjuvant to two New Zealand White male rabbits, 3 months of age. Boosts of 100 μg of antigen in Freund's incomplete adjuvant were given on average every five weeks and bleeds were drawn seven days after the second boost. One of the two resulting antisera, U104, was used here after affinity-purification on peptide antigen columns (21).

Epitope Tagging—To construct an epitope-tagged version of the murine cholesterol 25-hydroxylase enzyme, a cDNA fragment spanning the coding region and having BspDI and XbaI restriction sites at the 5' and 3' ends, respectively, was amplified by the polymerase chain reaction. The template was the plasmid pCMV-m25 and the thermocycler program consisted of 35 cycles of 94° C./30 sec; 57° C./15 sec; 72° C./60 sec. The amplif fragment was purified on a Centricon-100 column (Amicon Corp., Beverly, Mass.), digested with BspDI and XbaI, repurified by chromatography on a Centricon-100 column, and ligated into a modified pcDNA3 vector containing a sequence for a C-myc epitope in front of the BspDI site. The desired recombinant was termed pcDNA3-NH$_2$-myc-m25. This plasmid encodes a fusion protein in which the sequence containing two tandem copies of a C-myc epitope is linked to the amino terminus of the murine cholesterol 25-hydroxylase protein lacking the initial methionine residue. A similar strategy was used to place tandem C-myc epitopes at the amino terminus of the human cholesterol 25-hydroxylase cDNA, producing the plasmid pcDNA3-NH$_2$-myc-h25.

A double C-myc epitope was placed at the carboxy-terminus of the murine cholesterol 25-hydroxylase cDNA as follows. An oligonucleotide encoding these epitopes with an RsrII cohesive 5'-end and a blunt 3'-end was formed by annealing phosphorylated oligonucleotide primers as described (22). The annealed duplex was ligated into pCMV-m25 that had been digested with Eco47ff and Rsru and purified by agarose gel electrophoresis. The resulting plasmid, pCMV-m25-COOH-myc, encodes a protein comprising amino acids 1–267 of the murine cholesterol 25-hydroxylase fused to the two C-myc epitope sequences.

Mutagenesis—Site-directed mutagenesis (23) was carried out using a polymerase chain reaction-based kit (Quik-Change, Stratagene) on the plasmid pCMV-m25. The mutagenic oligonucleotide primers were designed to convert histidine codons at positions 242 and 243 of the murine protein to glutamine codons. Mutagenesis was carried out according to instructions provided by the manufacturer. Plasmid DNA products were subjected to DNA sequence analysis to confirm the presence of the substitution mutations and the absence of spurious mutations. The plasmid containing the desired mutations was named pCMV-m25-HH242QQ.

Measurement of cholesterol 25-hydroxylase activity in cell lysates—On day 0, a derivative of Chinese hamster ovarian cells expressing the polyoma virus middle T antigen (31) (CHOP cells) were plated at a density of 750,000 cells/100 mm dish in Medium C (1:1 (v/v) DMEM: Ham's F12 medium containing 5% fetal calf serum, 100 u/ml penicillin, and 100 $\mu$g/ml streptomycin sulfate). On day 1, the cells were transfected with 1.5 $\mu$g of pVA-1 and 13.5 $\mu$g of pCMV6, pCMV-m25-HH242QQ, or pCMV-m25 per dish for vector, mutant, and wild-type 25-hydroxylase transfections, respectively. 60 $\mu$l of pfx-8 lipid was used as a transfection reagent as described above. On day 2, cells were incubated for 1 hour with 2% (w/v) 2-hydroxypropyl-$\beta$-cyclodextrin dissolved in a 1:1 solution of DMEM/Ham's F12 medium. The cells were washed once with ice-cold PBS and then harvested in the same buffer using a rubber policeman. After centrifugation at 1000×g for 5 minutes, the buffer was aspirated and the cell pellet was resuspended in 1 ml of 50 mM potassium phosphate buffer, pH 7.4, containing protease inhibitors (Boehringer Complete Mini, EDTA-free, at the concentration recommended by the supplier). A cell lysate was prepared using a Polytron set at 10,000 rpm, with 3 bursts of 3 seconds each with 30 second intervals between bursts. Incubations were performed at 37° C. with 140 $\mu$g of cell lysate protein in 50 mM potassium phosphate buffer, pH 7.4, containing 5 mM NADPH. [4-$^{14}$C] Cholesterol was added in 4 $\mu$l of 45% (w/v) 2-hydroxypropylcyclodextrin in water to a final concentration of 5 $\mu$M. The total volume of the incubation was adjusted to 200 $\mu$l. After 2 h, reactions were extracted with chloroform-methanol (2:1, v/v) and analyzed by thin layer chromatography.

SREBP Cleavage Assay—Stock cultures of CHO-7 cells, a subline of CHO-K1 cells selected for growth in lipoprotein-deficient serum (25), were maintained in Medium D (1:1 (v/v) DMEM: Ham's F12 medium containing 5% newborn calf lipoprotein-poor serum, 100 U/ml penicillin, and 100 $\mu$g/ml streptomycin sulfate). On day 0, cells were plated at a density of 7×10$^5$ cells/60 mm dish. On day 1, transfections were carried out using 4 $\mu$g/dish of the indicated plasmid DNA and Lipofectamin reagent (Life Technologies) according to the manufacturer's instructions and with modifications as described (26). After transfection, fresh media supplemented with 50 $\mu$M mevalonate, 50 $\mu$M compactin and 0.2% ethanol containing either no sterol or a mixture of sterols (final concentrations of 1 $\mu$g/ml 25-hydroxycholesterol and 10 $\mu$g/ml cholesterol) were added. The cells were returned for 20 h to a 37° C. incubator, harvested, and then fractionated into a nuclear extract and a 10$^5$×g membrane pellet as described (27). Immunoblot analyses of SREBP-1 and -2 proteins were performed using a SuperSignal Substrate kit (Pierce) and the murine monoclonal antibodies IgG-2A4 and IgG-7D4 (28,29).

Gas-Chromatography-Mass Spectrometry—Six-well plates of CHOP cells were transfected with pCMV-m25 or with vector alone as described above, and incubated for 48 h in Medium D supplemented with 10 $\mu$g/ml cholesterol. Thereafter, media were extracted with chloroform:methanol (2:1, v/v; 5 ml/well), and the organic phase was separated and taken to dryness under a stream of nitrogen. Extracts from 6 wells were combined for subsequent procedures. The samples were purified on Isolute Silica columns (International Sorbent Technology, Mid Glamorgan, UK) and hydroxyl groups were converted to trimethylsilyl ethers as previously described (13).

Gas chromatography mass spectrometry was performed on a Varian 3400 gas chromatograph equipped with an HP-5MS capillary column (30 m×0.25 mm, 0.25 $\mu$m phase thickness) connected to a Finnigan SSQ700 mass spectrometer. The gas chromatography temperature program was: 180° C. for 1 min., followed by a temperature gradient of 10° C./min to 300° C., and a final elution at 300° C. for 15 minutes. Helium was used as the carrier gas at an injector valve pressure of 6 psi. Injector and transfer line temperatures were set to 280° C., and the injector was operated in the splitless mode. The machine was operated in the electron ionization mode with electron energy set to 70 eV, and the quadrupole was scanned between m/z 100–500 at a rate of 1 scan/1.5 seconds.

Analysis of N-Linked Carbohydrates—To examine the sensitivity of N-linked carbohydrates on cholesterol 25-hydroxylase to endoglycosidase digestion, COS M6 cells were initially plated at a density of 5×10$^5$ cells/60 mm dish in Medium A on Day 0 of the experiment. On Day 1, one dish each was transfected with 4.5 $\mu$g pCMV-m25, pcDNA3-NH$_2$-myc-m25, pCMV-m25-COOH-myc, pCMV-h25, or pcDNA3-NH$_2$-myc-h25, together with 0.5 $\mu$g of pVA1 and 20 $\mu$l of pfx-8 lipid as described above. After transfection, cells were cultured in Medium B. On day 2, cells were harvested using a rubber policeman, pelleted at 1000×g, washed with 1 ml of phosphate buffered saline (pH 7.4), and resuspended in 0.2 ml of a buffer containing 10 mM Tris-Cl, pH 8.0 and 1 mM EDTA. Cells were lysed by 20 passages through a 22 gauge needle and aliquots of the lysates (10 $\mu$l, ~40 $\mu$g protein) were treated with endoglycosidase H or peptide N-glycosidase (PNGase) F overnight in a volume of 30 µl according to the instructions given by the supplier (New England Biolabs, Beverly, Mass.). One volume of 2 X Laemmli gel loading buffer was then added to each sample, followed by incubation at 100° C. for 10 minutes and electrophoresis through a 12% polyacrylamide-SDS gel for 16 h at constant current (10 mA). Separated proteins were electroblotted to PVDF membranes (30), which were incubated with affinity-purified (21) antipeptide antibody directed against cholesterol 25-hydroxylase (U-104, see above) at 0.8 µg/ml. A goat anti-rabbit horseradish peroxidase-conjugated antibody (Amersham, Arlington Heights, Ill.) was used as secondary antibody and visualization was via an ECL Plus kit (Amersham).

Cytochemistry—For indirect immunocytochemistry, COS M6 cells were plated at a density of $4 \times 10^4$ cells per well on glass coverslips placed in 6-well dishes containing Medium B. On Day 1, cells were transfected with either a vector alone control (pCMV6) or with pCMV-m25-COOH-myc-m25 or pcDNA3-NH$_2$-myc-m25. Three pg of plasmid DNA and 12 µl of pfx-8 lipid were used per well. After transfection, cells were cultured in Medium B. Indirect immunocytochemistry was then performed with the indicated antibody and lectin probes as follows. Cells were fixed for 30 min with 3% (w/v) paraformaldehyde in Hank's balanced salt solution (pH 7.4). Following fixation, the coverslips were briefly rinsed with PBS (0.1 M phosphate buffer, pH 7.4, 0.15 M NaCl), and free aldehyde groups were quenched by incubation in PBS containing 50 mM NH$_4$Cl for 30 min. Permeabilization was accomplished by incubation in 0.1% (v/v) Triton X-100 in H$_2$O for 7 min on ice, followed by rinsing in PBS containing 1% (w/v) bovine serum albumin (blocking buffer) for 30 min at room temperature. Coverslips were incubated with rabbit anti-C-myc IgG (Upstate Biotechnology Inc., 10 µg/ml in blocking buffer) for 2 h at room temperature. Finally, coverslips were incubated with FITC-goat anti-rabbit IgG (Zymed; 20 µg/ml in blocking buffer) for 1 h at room temperature. For Golgi compartment staining, rhodamine-labeled wheat germ agglutinin was added during the second antibody incubation at a concentration of 1.25 µg/ml. Coverslips were washed three times with PBS containing 0.1% BSA after each antibody or lectin incubation. Cells were photographed using a Zeiss Photomicroscope.

Inhibitor Studies—Transfection of CHOP cells was carried out as described above with the following exceptions. Cells were plated on Day 0 at a density of 150,000 cells/well in 6-well plates containing Medium C. On Day 1, cells were transfected with 2.7 µg of the indicated cholesterol 25-hydroxylase expression plasmid and 0.3 µg of pVA-1, using 12 µl of pfx-8 as transfection lipid. After 4 h, the lipid-DNA mixture was removed and 1.5 ml of Medium D was added. In certain experiments, this medium was aspirated and replaced on Day 2 with 1 ml per well of a 20 mg/ml solution of 2-hydroxypropyl-β-cyclodextrin (Sigma) in DMEM/Ham's F12 (1:1) medium and returned to the incubator. The cyclodextrin containing medium was replaced after 1–1.5 h with 1.5 ml of Medium D, and substrate and inhibitors were then added, each in a volume of 4.5 µl of ethanol. The concentration of [4-$^{14}$C]cholesterol substrate (specific activity=26.8 mCi/mmol) was 3 µM. Inhibitors were added to final concentrations of 3, 10 or 30 µM. Cells and/or cells plus medium were harvested at the indicated times, extracted, and the conversion of substrate into [4-$^{14}$C]25-hydroxycholesterol product was determined by thin layer chromatography as described above. The inhibitors used were cholesterol(5-cholesten-3β-ol), cholestanol (5α-cholestan-3β-ol), epicholesterol (5-cholesten-3α-ol), coprostanol(5β-cholestan-3β-ol), desmosterol(5,24-cholestadien-3β-ol), β-sitosterol(5-cholesten-24β-ethyl-3β-ol ), 25-hydroxycholesterol (cholest-5-ene-3β,25-diol), and 27-nor-25-oxocholesterol (27-nor-25-oxo-5-cholesten-3β-ol). All steroids were purchased from Steraloids Inc. (Wilton, N.H.), except cholesterol, which was from Sigma (St. Louis, Mo.).

Stable cell lines—EcR-CHO cells (Invitrogen), a cell line stably expressing the subunits of the Drosophila ecdysone receptor, RXR and VgECR (31) were plated on day 0 at a density of 500,000 cells/100 mm dish in Medium C supplemented with 250 µg/ml zeocin. On day 1, cells were transfected with 5 µg of pIND-m25 using 15 µl of Fugene 6 (Boehringer-Mannheim) according to the instructions of the manufacturer. The plasmid pIND-m25 was constructed by insertion of a full-length mouse 25-hydroxylase cDNA fragment from plasmid pCMV-m25 into the pIND vector (Invitrogen). On day 2, cells were split 1:15 and plated in fresh Medium C supplemented with 250 µg/ml Zeocin and 700 µg/ml geneticin. Cells were refed this medium every second day, and on day 10, groups of five geneticin-resistant colonies were replated in individual wells. Following expansion, cells were tested for cholesterol 25-hydroxylase expression by addition of ponasterone (Invitrogen) to a final concentration of 5 µM (16h), followed by immunoblot analysis of total cell protein. Antibody U104 (affinity-purified) was used to detect expression of the enzyme as described above. One positive group of cells was selected and subcloned though one additional round to ensure clonality. One of the resulting cell strains, designated TR3102a, which manifest high level expression of cholesterol 25-hydroxylase upon ponasterone induction, and another, designated TR3102g, with no detectable inducible enzyme expression, were selected and maintained as lines. For routine induction experiments, 10 µM ponasterone was used for the indicated time periods.

Cholesterol biosynthesis—TR3102a and TR3102g cells were plated on day 0 at a density of 250,000 cells/60 mm dish in Medium C containing zeocin and geneticin as above. On day 1, the medium was changed to Medium F (Medium D containing 250 µg/ml Zeocin, 700 µg/ml geneticin, and 10 µM ponasterone). On day 2, 20 µl of an aqueous solution containing 15 µCi of [1,2-$^{14}$C]acetate (American Radiolabeled Chemicals), adjusted with cold acetate to a final mass of 1 µmol, was added to each dish. The additions were made in a staggered fashion so that all cells were harvested at the same time, corresponding to incubation times of 2, 4, and 6 h, respectively. The total time of induction with ponasterone was 27 h, including the acetate labeling period. Nonsaponifiable lipids were isolated and analyzed by thin layer chromatography as described (32) except that 5 µCi of [26, 27-$^3$H]25-hydroxycholesterol (New England Nuclear) was used as a standard. Quantification of acetate incorporation into cholesterol was via phosphoimage analysis.

RESULTS

The livers of transgenic mice overexpressing the transcription factor SREBP-1a accumulate large quantities of cholesterol and triglycerides, owing to the overproduction of lipid synthesizing enzymes (14). An analysis of stool lipids by mass spectrometry revealed that these animals also excrete high levels of several oxysterols, including 25-hydroxycholesterol. To isolate cDNAs that encode putative oxysterol synthesizing enzymes from the livers of these transgenic mice, an expression cloning strategy in cultured mammalian cells was conceived and optimized. The basic premise of the screen was to transfect cells with pools of hepatic cDNAs cloned into an expression vector, add [$^{14}$C] cholesterol to the medium, and then measure the conversion of this substrate into oxysterols by thin layer chromatography assay. Initially, we used a previously isolated sterol 27-hydroxylase cDNA, whose encoded enzyme converts cholesterol into the oxysterol 27-hydroxycholesterol (15), to optimize assay parameters.

Chromatography studies with oxysterol standards revealed that the separation between cholesterol and some oxysterols was poor on silica gel plates. Furthermore, in control transfection studies with the sterol 27-hydroxylase expression vector, the strong phosphoimage signal from the substrate often obscured a weaker product signal. To overcome these problems, a cDNA encoding a murine oxysterol 7α-hydroxylase (18) was cotransfected into the cells. This addition should result in the conversion of oxysterol products to their 7α-hydroxylated forms. The oxysterol 7α-hydroxylase also possesses a minor 2-hydroxylase activity against 7α-hydroxylated sterols (18), thus the formation of 2,7α-hydroxylated oxysterols was expected. Both of these classes of hydroxylated oxysterols were readily separated from cholesterol by thin layer chromatography. The optimum transfection host (293 cells), transfection method (lipofection with pfx-8 lipid), and transient expression time (60 h) were determined. Further experiments confirmed that the sterol 27-hydroxylase enzyme, which is located in the mitochondria (15), was stimulated two- to three-fold when a cDNA encoding the murine steroidogenic acute regulatory protein was cotransfected into cells (16,33). Finally, addition of the adenovirus VA1 gene, which enhances the translation of mRNAs transcribed from transfected plasmids (19), to the DNA cocktail stimulated expression levels another 1.5-fold. Under these optimized conditions, sterol 27-hydroxylase enzyme activity could be detected over background when the cDNA expression vector was diluted 3,000–5,000-fold.

A library consisting of 1.5×10$^6$ individual cDNAs was next constructed in a pCMV6 vector using poly(A)$^+$ mRNA isolated from an SREBP-1a transgenic mouse liver. Two hundred fifty-five aliquots of ~3,800 individual plasmids from the library were screened using the optimized parameters described above. Data from transfection experiments revealed several positive cDNA pools. In one gel, the pool analyzed in lane 1 did not contain a cDNA encoding a cholesterol metabolizing enzyme. However, the pools analyzed in lanes 2–5 produced low to very low levels of two sterols that migrated more slowly and thus were more hydrophilic than the cholesterol substrate. Additional experiments revealed that the pools analyzed in lanes 2–4 contained sterol 27-hydroxylase cDNAs, whereas that analyzed in lane 5 contained a cholesterol 25-hydroxylase cDNA.

The pool containing the 25-hydroxylase cDNA was progressively subdivided and expressed to isolate a single cDNA. As the purity of the cDNA increased, the level of product generated in the transfected cells also increased to the point that cotransfection of the oxysterol 7α-hydroxylase cDNA was dispensable. Additional experiments revealed that the cDNA-encoded enzyme was not stimulated by inclusion of the steroidogenic acute activator cDNA, suggesting that it was not a mitochondrial protein. Transfection of the pure cDNA into CHOP cells produced abundant 25-hydroxylase enzyme activity that increased with time of incubation. The activity was stimulated approximately 10-fold by treatment of transfected cells with 2-hydroxypropyl-β-cyclodextrin. This compound presumably removes endogenous cholesterol from the membranes of the transfected cells that otherwise competes with the exogenously added radiolabeled cholesterol substrate (34).

The chemical structure of the oxysterol produced by the isolated cDNA was determined by gas chromatography-electron ionization mass spectrometry. The media from cells transfected with the putative cholesterol 25-hydroxylase cDNA contained a prominent sterol eluting at 23.56 minutes from the gas chromatography column. This sterol was not present in the media of mock-transfected cells. The mass spectrum of the cDNA-generated product was virtually identical to that of an authentic 25-hydroxycholesterol standard.

A search of the DNA data bases revealed a human EST with partial sequence similarity to the murine 25-hydroxylase cDNA. This EST was used to isolate a near full-length cDNA encoding the human 25-hydroxylase as described in Experimental Procedures. Transfection into 293 cells of the human cDNA cloned in a pCMV6 vector produced abundant 25-hydroxylase enzyme activity. This activity was stimulated approximately five-fold by treatment of cells with 2-hydroxypropyl-β-cyclodextrin.

Alignments of the genomic DNA and deduced amino acid sequences of the murine and human cholesterol 25-hydroxylases reveal that the two proteins share 78% sequence identity, while the encoding cDNAs are 82% identical in their translated regions.

The predicated molecular weights of the murine and human enzymes are 34,700 and 31,700, respectively. The most notable difference between the two is a 26-amino acid extension at the carboxy-terminus of the murine enzyme that is not present in the human enzyme. Both proteins have three clusters of conserved histidine residues (amino acids 143–147, 157–161, and 238–243 in the murine sequence). Similar clusters of histidine residues are present in a Pseudomonas alkane hydroxylase and xylene monooxygenase (35,36), the eukaryotic stearoyl-CoA desaturases (37), and the yeast and human C-4 sterol methyl oxidases (38,39). These enzymes are members of a family of proteins that utilize diiron cofactors to catalyze diverse reactions on hydrophobic substrates. Hydropathy analyses of the 25-hydroxylase sequences revealed four conserved regions of extended hydrophobicity that can constitute as many as eight transmembrane domains. The location of the first, second, and fourth of these hydrophobic regions coincided with similar sequences in the Pseudomonas alkane hydroxylase, which contains six transmembrane domains (40).

To determine if the clustered histidine residues were important for enzyme activity, a pair of histidine codons at positions 242 and 243 in the murine protein were changed to glutamine codons by site-directed mutagenesis of the wild type cDNA. The resulting mutant cDNA was transfected into CHOP cells and assayed for expression of the protein and for cholesterol 25-hydroxylase enzyme activity. Mutation of the two histidine residues had no effect on steady state expression levels as judged by immunoblotting but eliminated enzyme activity in transfected cells. Similar results were obtained in a second experiment in which cholesterol 25-hydroxylase enzyme activity was measured in cell lysates rather than in intact cells.

The subcellular localization of cholesterol 25-hydroxylase was assessed in two ways. First, the presence and structure of asparagine-linked carbohydrates were analyzed by endoglycosidase digestion. Expression of murine or human cDNAs in COS cells produced two forms of the enzyme that differed in mass by approximately 3 kDa as judged by immunoblotting. When total membrane proteins from transfected cells were digested with endoglycosidase H or peptide: N-glycosidase F, only a single form of cholesterol 25-hydroxylase was detected that migrated with the lower molecular mass enzyme of untreated cells. These data suggested that cholesterol 25-hydroxylase was present in the membrane fraction of the cell and that some of the molecules were glycosylated with high-mannose, asparagine-linked carbohydrates. In agreement with these results, the sequence of the murine enzyme contains two potential sites for N-linked glycosylation (amino acids 5 and 163), and the human enzyme sequence contains three such sites (amino acids 5, 163, and 189).

The second approach employed immunocytochemistry. Simian COS cells were transfected with the plasmid pCMV-m25-COOH-myc, which encodes a carboxyl-terminal, C-Myc epitope-tagged version of the murine cholesterol 25-hydroxylase. After a transient expression period, cells were permeabilized and recombinant cholesterol 25-hydroxylase detected by indirect immunocytochemistry using a fluorescein-labeled secondary antibody. At the same time, the transfected cells were stained with rhodamine-labeled wheat germ agglutinin (Sigma, #L5266), a lectin that binds to glycoproteins concentrated in the Golgi compartment. Fluorescein signal (green) representing cholesterol 25-hydroxylase was detected in the endoplasmic reticulum and a perinuclear compartment of transfected cells. The perinuclear compartment was identified as the Golgi apparatus based on colocalization with the wheat germ agglutinin lectin (red rhodamine signal). Similar results were obtained when the C-Myc epitope was placed at the amino-terminus of the expressed murine enzyme.

We next isolated the murine and human cholesterol 25-hydroxylase genes. DNA sequence analysis of the isolated genomic DNAs and comparison to the respective cDNA sequences revealed that both genes lacked introns. This structure was confirmed by Southern blotting analyses of murine and human DNA and by direct amplification of the genes from genomic DNA. Transfection into 293 cells of a plasmid containing the genomic DNA insert from the bacteriophage λ clone that encompassed 10 kb of 5'-flanking DNA and ~3 kb of 3' flanking DNA of the human 25-hydroxylase gene resulted in the expression of enzyme activity, which indicated that the isolated gene was not a pseudogene and that requisite regulatory sequences were located close to the coding region. The human gene was localized to chromosome 10q23.3 by somatic and radiation hybrid DNA panel mapping and fluorescence in situ hybridization.

The tissue distribution of the murine cholesterol 25-hydroxylase mRNA was assessed by blot hybridization. Low levels of a 1.5 kb mRNA were present in the heart, lung, and kidney. The mRNA was not be detected in the livers of control mice, however it was present in RNA from the liver of the SREBP-1a transgenic mouse used to prepare the original cDNA expression library. RNA blotting experiments using commercially available filters revealed only very low levels of human cholesterol 25-hydroxylase mRNA in 16 different tissues.

The potent regulatory effects of 25-hydroxycholesterol were first observed in assays that measured the suppressive effects of oxysterols on cholesterol synthesis (1,2). To determine if the 25-hydroxycholesterol synthesized by the 25-hydroxylase enzyme could suppress cholesterol synthesis, a line of CHO cells containing an ecdysone-inducible 25-hydroxylase cDNA was isolated as described in Experimental Procedures. These cells, and a control cell line that did not contain the 25-hydroxylase cDNA, were induced with the ecdysone analog ponasterone and the incorporation of [$^{14}$C] acetate into cholesterol was measured as a function of time. Induction with ecdysone led to a marked reduction of cholesterol synthesis in cells containing the 25-hydroxylase cDNA but had no effect on this parameter in the control cells.

Experiments were carried out to determine if expression of cholesterol 25-hydroxylase in transfected cells affected the processing of SREBP transcription factors. Cultured CHO-7 cells were transiently transfected with either vector alone or an expression vector containing the murine 25-hydroxylase cDNA. After 24 h, fractions enriched in membrane or nuclear proteins were prepared from the transfected cells. Equal amounts of protein from each subcellular compartment were separated by gel electrophoresis and the levels of SREBP-1 and -2 were determined by immunoblotting. Mock-transfected cells grown in the absence of sterols to induce SREBP-1 cleavage contained intact, uncleaved SREBP-1 in the membrane fraction and cleaved SREBP-1 in the nuclear fraction. Mock-transfected cells grown in the presence of sterols (cholesterol plus 25-hydroxycholesterol) contained a majority of the immunodetectable SREBP-1 in the membrane fraction. Cells transfected with the 25-hydroxylase cDNA and grown in the absence of sterols contained a majority of SREBP-1 in the membrane fraction even though no exogenous sterols were added, presumably because the 25-hydroxycholesterol produced by the expressed 25-hydroxylase suppressed cleavage of the transcription factor. Similar results were obtained when the processing of SREBP-2 was followed by subcellular fractionation and immunoblotting.

We next tested the ability of different sterols to inhibit cholesterol 25-hydroxylase. In these experiments, 293 cells were transfected with a 25-hydroxylase cDNA, treated with 2-hydroxypropyl-β-cyclodextrin to remove endogenous cholesterol, and then incubated with 3 $\mu$M [$^{14}$C]cholesterol and the indicated concentrations of unlabeled inhibitor sterol. The rank order of inhibition for the nine sterols tested was desmosterol>cholestanol>25-hydroxycholesterol >epicholesterol>sitosterol>>coprostanol=25-oxo-27-nor-cholesterol. When desmosterol and [$^{14}$C]cholesterol were present in equimolar amounts (3 $\mu$M), enzyme activity was decreased by 30%, whereas coprostanol did not inhibit the enzyme at this concentration. The observed inhibition of 25-hydroxylase activity could be due to individual sterols acting as either true inhibitors of the enzyme (i.e., not as substrates) or as competitors of the cholesterol substrate. In the case of desmosterol (5,24-cholestadien-3β-ol), which can not be 25-hydroxylated due to the $\Delta^{24}$ bond, this sterol appears to act as a true inhibitor.

REFERENCES

1. Kandutsch, A. A., and Chen, H. W. (1974) *J. Biol. Chem.* 249, 6057–6061
2. Brown, M. S., and Goldstein, J. L. (1974) *J. Biol. Chem.* 249, 7306–7314
3. Björkhem, I., Andersson, O., Diczfalusy, U., Sevastik, B., Xiu, R., Duan, C., and Lund, E. (1994) *Proc. Natl. Acad. Sci. U.S.A.* 91, 8592–8596
4. Babiker, A., Andersson, O., Lund, E., Xiu, R.-J., Deeb, S., Reshef, A., Leitersdorf, E., Diczfalusy, U., and Björkhem, I. (1997) *J. Biol. Chem.* 272, 26253–26261
5. Lutjohann, D., Breuer, O., Ahlborg, G., Nennesmo, I., Siden, A., Diczfalusy, U., and Björkhem, I. (1996) *Proc. Natl. Acad. Sci.* USA 93, 9799–9804
6. Schwarz, M., Lund, E. G., and Russell, D. W. (1998) *Current Opinion in Lipidology* 9, 1–6

7. Ishibashi, S., Schwarz, M., Frykman, P. K., Herz, J., and Russell, D. W. (1996) *J. Biol. Chem.* 271, 18017–18023
8. Janowski, B. A., Willy, P. J., Devi, T. R., Falck, J. R., and Mangelsdorf, D. J. (1996) *Nature* 383, 728–731
9. Lehmann, J. M., Kliewer, S. T., Moore, L. B., Srnith-Oliver, T. A., Oliver, B. B., Su, J., Sundseth, S. S., Winegar, D. A., Blanchard, D. E., Spencer, T. A., and Willson, T. M. (1997) *J. Biol. Chem.* 272, 3137–3140
10. Russell, D. W., and Setchell, K. D. R. (1992) *Biochemistry* 31, 4737–4749
11. Peet, D. J., Turley, S. D., Ma, W., Janowski, B. A., Lobaccaro, J.-M. A., Hammer, R. E., and Mangelsdorf, D. J. (1998) *Cell* 93, 693–704
12. Brown, M. S., and Goldstein, J. L. (1997) *Cell* 89, 331–340
13. Dzeletovic, S., Breuer, O., Lund, E., and Diczfalusy, U. (1995) *Anal. Biochem.* 225, 73–80
14. Shimano, H., Horton, J. D., Hamrner, R. E., Shimomura, I., Brown, M. S., and Goldstein, J. L. (1996) *J. Clin. Invest.* 98, 1575–1584
15. Andersson, S., Davis, D. L., Dahlbäck, H., Jörnvall, H., and Russell, D. W. (1989) *J. Biol. Chem.* 264, 8222–8229
16. Stocco, D. M., and Clark, B. J. (1996) *Endocrine Rev.* 17, 221–244
17. Stapleton, G., Steel, M., Richardson, M., Mason, J. O., Rose, K. A., Morris, R. G. M., and Lathe, R. (1995) *J. Biol. Chem.* 270, 29739–29745
18. Schwarz, M., Lund, E. G., Lathe, R., Bjorkhem, I., and Russell, D. W. (1997) *J. Biol. Chem.* 272, 23995–24001
19. Schneider, R. J., and Shenk, T. (1987) *Ann. Rev. Biochem.* 56, 317–332
20. Sambrook, J., Fritsch, E. F., and Maniatis, T. (1989), *Molecular Cloning*, Cold Spring Harbor Laboratory Press, New York, N.Y.
21. Harlow, E., and Lane, D. (1988) *Antibodies, A Laboratory Manual*, Cold Spring Harbor Laboratory Press, New York, N.Y.
22. Hua, X., Sakai, J., Ho, Y. K., Goldstein, J. L., and Brown, M. S. (1995) *J. Biol. Chem.* 270, 29422–29427
23. Smith, M. (1985) *Ann. Rev. Genetics* 19, 423–462
24. Heffernan, M., and Dennis, J. W. (1991) *Nuc. Acids Res.* 19, 85–92
25. Metherall, J. E., Goldstein, J. L., Luskey, K. L., and Brown, M. S. (1989) *J. Biol. Chem.* 264, 15634–15641
26. Rawson, R. B., Zelenski, N. G., Nijhawan, D., Ye, J., Sakai, J., Hasan, M. Z., Chang, T. Y., Brown, M. S., and Goldstein, J. L. (1997) *Mol. Cell* 1, 47–57
27. Sakai, J., Duncan, E. A., Rawson, R. B., Hua, X., Brown, M. S., and Goldstein, J. L. (1996) *Cell* 85, 1037–1046
28. Hua, X., Nohturfft, A., Goldstein, J. L., and Brown, M. S. (1996) *Cell* 87, 415–426
29. Yang, J., Brown, M. S., Ho, Y. K., and Goldstein, J. L. (1995) *J. Biol. Chem.* 270, 12152–12161
30. Thigpen, A. E., Silver, R. I., Guileyardo, J. M., Casey, M. L., McConnell, J. D., and Russell, D. W. (1993) *J. Clin. Invest.* 92, 903–910
31. No, D., Yao, T. P., and Evans, R. M. (1996) *Proc. Natl. Acad. Sci., U.S.A.* 93, 3346–3351
32. Goldstein, J. L., and Brown, M. S. (1973) *Proc. Natl. Acad. Sci., U.S.A.* 70, 2804–2808
33. Sugawara, T., Lin, D., Holt, J. A., Martin, K. O., Javitt, N. B., Miller, W. L., and Strauss, J. F. Jr. (1995) *Biochemistry* 34, 12506–12512
34. Kilsdonk, E. P. C., Yancey, P. G., Stoudt, G. W., Bangerter, F. W., Johnson, W. J., Phillips, M. C., and Rothblat, G. H. (1995) *J. Biol. Chem.* 270, 17250–17256
35. Suzuki, M., Hayakawa, T., Shaw, J. P., Rekik, M., and Harayama, S. (1991) *J. Bacteriol.* 173, 1690–1695
36. Kok, M., Oldenhuis, R., van der Linden, M. P. G., Raatjes, P., Kingma, J., van Lelyveld, P. H., and Witholt, B. (1989) *J. Biol. Chem.* 264, 5435–5441
37. Shanklin, J., Whittle, E., and Fox, B. G. (1994) *Biochemistry* 33, 12787–12794
38. Bard, M., Bruner, D. A., Pierson, C. A., Lees, N. D., Bierman, B., Frye, L., Koegel, C., and Barbuch, R. (1996) *Proc. Natl. Acad. Sci., U.S.A.* 93, 186–190
39. Li, L., and Kaplan, J. (1996) *J. Biol. Chem.* 271, 16927–16933
40. van Beilen, J. B., Penninga, D., and Witholt, B. (1992) *J. Biol. Chem.* 267, 9194–9201
41. Fox, B. G., Shanklin, J., Ai, J., Loehr, T. M., and Sanders-Loehr, J. (1994) *Biochemistry* 33, 12776–12786.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated human cholesterol 25-hydroxylase.

2. An isolated mouse cholesterol 25-hydroxylase.

3. A cholesterol 25 hydroxylase according to claim 1 comprising an amino acid sequence of SEQ ID NO:2.

4. A cholesterol 25-hydroxylase according to claim 2 comprising an amino acid sequence of SEQ ID NO:4.

5. A recombinant expression vector encoding and expressing a human cholesterol 25-hydroxylase.

6. A recombinant expression vector encoding and expressing a mouse cholesterol 25-hydroxylase.

7. A recombinant expression vector according to claim 5 comprising a human cholesterol 25-hydroxylase cDNA sequence.

8. A recombinant expression vector according to claim 6 comprising a mouse cholesterol 25-hydroxylase cDNA sequence.

9. A recombinant expression vector comprising a recombinant regulator of gene expression comprising a mouse cholesterol 25-hydroxylase promoter having cis transcriptional regulatory activity.

10. A recombinant expression vector according to claim 9 comprising a reporter gene other than a cholesterol 25-hydroxylase gene operatively joined to said regulator.

11. A host cell comprising an expression vector according to claim 5.

12. A host cell comprising an expression vector according to claim 6.

13. A host cell comprising an expression vector according to claim 10.

14. A method of making a cholesterol 25-hydroxylase, said method comprising steps; introducing a vector according to claim 5 into a host cell or cellular extract, incubating said host cell or extract under conditions whereby said vector is expressed as a transcript and said transcript is expressed as a translation product comprising said cholesterol 25-hydroxylase, and isolating said translation product.

15. A method of making a cholesterol 25-hydroxylase, said method comprising steps: introducing a vector according to claim 6 into a host cell or cellular extract, incubating said host cell or extract under conditions whereby said vector is expressed as a transcript and said transcript is expressed as a translation product comprising said cholesterol 25-hydroxylase, and isolating said translation product.

16. A method of screening for an agent that modulates the interaction of a cholesterol 25-hydroxylase polypeptide to a binding target, said method comprising the steps of:

incubating a mixture comprising:
an isolated cholesterol 25-hydroxylase according to claim 1,
a binding target of said polypeptide, and
a candidate agent;
under conditions whereby, but for the presence of said agent, said polypeptide specifically binds said binding target at a reference affinity;
detecting the binding affinity of said polypeptide to said binding target to determine an agent-biased affinity,
wherein a difference between the agent-biased affinity and the reference affinity indicates that said agent modulates the binding of said polypeptide to said binding target.

17. A method of screening for an agent that modulates the interaction of a cholesterol 25-hydroxylase polypeptide to a binding target, said method comprising the steps of:

incubating a mixture comprising:
an isolated cholesterol 25-hydroxylase according to claim 2,
a binding target of said polypeptide, and
a candidate agent;
under conditions whereby, but for the presence of said agent, said polypeptide specifically binds said binding target at a reference affinity;
detecting the binding affinity of said polypeptide to said binding target to determine an agent-biased affinity,
wherein a difference between the agent-biased affinity and the reference affinity indicates that said agent modulates the binding of said polypeptide to said binding target.

18. A method according to claim 16, wherein said cholesterol 25-hydroxylase is expressed from an expression vector in a cell.

19. A method according to claim 17, wherein said cholesterol 25-hydroxylase is expressed from an expression vector in a cell.

20. A method according to claim 16, wherein said cholesterol 25-hydroxylase is expressed from an expression vector in a cell and said mixture is in said cell.

21. A method according to claim 17, wherein said cholesterol 25-hydroxylase is expressed from an expression vector in a cell and said mixture is in said cell.

22. A method according to claim 16, wherein said cholesterol 25-hydroxylase is expressed from an expression vector in a cell, said mixture is in said cell and said binding target comprises cholesterol.

23. A method according to claim 17, wherein said cholesterol 25-hydroxylase is expressed from an expression vector in a cell, said mixture is in said cell and said binding target comprises cholesterol.

24. method according to claim 16 wherein said cholesterol 25-hydroxylase is expressed from an expression vector in a cell, said mixture is in said cell, said binding target comprises cholesterol and said detecting comprises detecting the conversion of said cholesterol into 25-hydroxy cholesterol.

25. A method according to claim 17, wherein said cholesterol 25-hydroxylase is expressed from an expression vector in a cell, said mixture is in said cell, said binding target comprises cholesterol and said detecting comprises detecting the conversion of said cholesterol into 25-hydroxy cholesterol.

26. A method for identifying an agent that regulates the activity of a cholesterol 25-hydroxylase promoter, said method comprising steps:

contacting a cell comprising an expression vector according to claim 10 with a candidate agent, under conditions wherein, but for the presence of said agent, said reporter gene exhibits a first expression;

detecting the presence of a second expression of said reporter gene;

wherein a difference between said first and said second expression indicates said agent regulates the activity of a cholesterol 25-hydroxylase gene promoter.

27. A method according to claim 26, wherein said detecting step comprises detecting a calorimetric or luminescent signal of a gene product of said reporter gene.

28. A method according to claim 26 wherein said gene is detected by hybridization to a nucleic acid specific for said gene.

* * * * *